United States Patent [19]

Carson et al.

[11] Patent Number: 5,068,177

[45] Date of Patent: Nov. 26, 1991

[54] ANTI-IDIOTYPE ANTIBODIES INDUCED BY SYNTHETIC POLYPEPTIDES

[75] Inventors: Dennis A. Carson, Del Mar; Sherman Fong; Pojen P. Chen, both of San Diego, all of Calif.

[73] Assignee: Scripps Clinic and Research Foundation, La Jolla, Calif.

[21] Appl. No.: 762,698

[22] Filed: Aug. 5, 1985

Related U.S. Application Data

[63] Continuation-in-part of Ser. No. 566,172, Dec. 28, 1983, abandoned.

[51] Int. Cl.$^5$ .................. G01N 33/53; G01N 33/543; C07K 15/14; C07K 7/00
[52] U.S. Cl. .................. 435/7.92; 435/810; 435/7.93; 435/965; 424/88; 436/509; 436/518; 436/539; 436/543; 436/547; 436/808; 514/2; 530/300; 530/324; 530/325; 530/326; 530/327; 530/328; 530/329; 530/330; 530/387
[58] Field of Search .................. 435/810; 436/808

[56] References Cited

U.S. PATENT DOCUMENTS

| | | | |
|---|---|---|---|
| 4,415,491 | 11/1983 | Vyas | 436/820 |
| 4,454,121 | 6/1984 | Beachey | 514/12 |
| 4,474,757 | 10/1984 | Arnon et al. | 424/89 |
| 4,474,765 | 10/1984 | De Castiglione et al. | 424/177 |
| 4,493,795 | 1/1985 | Nestor, Sr. et al. | 530/328 |
| 4,536,479 | 8/1985 | Vander-Mallie | 436/800 |

OTHER PUBLICATIONS

*Brain Peptides*, Krieger et al. eds., Chapter 38, pp. 961–974, John Wiley & Sons, New York (1983).
Smith and Pease, *CRC Critical Reviews in Biochemistry*, vol. 8, 317–400, CRC Press, Inc., Boca Raton, Fla. (1980).
Sternberg and Thornton, *Nature*, 271, 15–19 (1978).
Schultz et al., *Nature*, 250, 140–142 (1979).
Angos et al., *Biochimica et Biophysica Acta*, 439, 261–263 (1976).
Matthews, *Biochimica et Biophysica Acta*, 405, 442–451 (1975).
Atassi et al., *Proc. Natl. Acad. Sci. USA*, 80, 840–844 (1983).
Kunkel et al., *Science*, vol. 140:1218–1219 (1963).
Capra et al., *Proc. Natl. Acad. Sci. USA*, 71:4032 (1974).
Weigert et al., *J. Exp. Med.*, 139:137 (1974).
Klapper et al., *Ann. Immunol. (Inst. Pasteur)*, 127C, 261 (1976).
Schilling et al., *Nature*, 283, 35 (1980).
Capra et al., *Immunol. Today*, 3, 332 (1982).
Capra et al., *Immunol. Today*, 4, 177 (1983).
Sutcliffe et al., *Science*, 219, 660 (1983).
Kunkel et al., *J. Exp. Med.*, 137, 331 (1973).
Kunkel et al., *J. Exp. Med.*, 139, 128 (1974).
Andrews et al., *Proc. Natl. Acad. Sci., USA*, 78, 3799 (1981).
Carson et al., *Mol. Immunol.*, 20, 1081 (1983).
Pawlita et al., *J. Immunol.*, 129, 615 (1982).
Chen et al., *J. Exp. Med.*, 161, 323 (1985).
Pons-Estel et al., *J. Exp. Med.*, 160, 893 (1984).
Rajewsky et al., *Ann. Rev. Immunol.* 1, 569 (1983).
Sakano et al., *Nature*, 280, 288 (1979).
Max et al., *Proc. Natl. Acad. Sci. USA*, 76, 3450 (1979).
Early et al., *Cell*, 19, 981 (1980).
Sakano et al., *Nature*, 286, 676 (1980).
Sakano et al., *Nature*, 290, 562 (1981).
Sienbenlist et al., *Nature*, 294, 631 (1981).
Kurosawa et al., *J. Exp. Med.*, 155, 201 (1982).

(List continued on next page.)

*Primary Examiner*—Esther L. Kepplinger
*Assistant Examiner*—Florina B. Hoffer
*Attorney, Agent, or Firm*—Dressler, Goldsmith, Shore, Sutker & Milnamow, Ltd.

[57] ABSTRACT

Chemically synthesized polypeptides containing about 6 to 40 amino acid residues and having amino acid residue sequences that substantially correspond to the primary amino acid residue sequences of particular variable or hypervariable regions of immunoglobulins, when administered alone or as polymers or as conjugates bound to carriers, induce the production of anti-idiotype antibodies of predetermined specificities.

35 Claims, 18 Drawing Sheets

OTHER PUBLICATIONS

Rudikoff et al., *J. Exp. Med.,* 158, 1385 (1983).

Tonegawa, *Nature,* 302:575 (1983).

McMillan et al., Synthetic Idiotypes: The Third Hypervariable Region of Murine Anti-Dextran Antibodies, Cell, 35: 859 (1983).

Chen et al., Anti-Hypervariable Region Antibody Induced by a Defined Peptide: An Approach for Studying the Structural Correlates of Idiotypes, *Proc. Natl. Acad. Sci. USA,* 81:1784–1788 (1984).

Chen et al., Delineation of a Cross-Reactive Idiotype on Human Autoantibodies with Antibody Against a Synthetic Peptide, *J. Exp. Med.,* 159:1502–1511 (1984).

Chen, et al., Characterization of an Epibody, an Antiidiotype that Reacts with both the Idiotype of Rheumatoid Factors (RF) an the Antigen Recognized by RF, *J. Exp. Med.,* 161:323 (1985).

Smith et al., Production of Heterologous Antibodies Specific for Murine B-Cell Leukemia ($BCL_1$) Immunoglobulin by Immunization with Synthetic Peptides Homologous to Heavy Chain Hypervairable Regions, *Cancer Research,* 45:6119 (1985).

Thielemans et al., Syngeneic Antiidiotype Immune Responses to A.B Cell Lymphoma, Comparison Between Heavy Chain Hypervariable Region Peptides and Intact Ig as Immunogens, *J. Exp. Med.,* 162:19 (1985).

Ghose et al., Antibodies to the First Constant-Region Domain of the Murine $\mu$-Chain Induced by a Synthetic Peptide, *Molec. Immun.,* 22:1145 (1985).

Fong, et al., *J. Immunol., vol. 131, No. 2, (1983), pp. 719–724.*

Lerner, R. A., Nature, vol. 299, (1982), pp. 592–596.

FIG.3

AMINO ACID RESIDUE SEQUENCES (CORRESPONDING TO PSL2)
OF SEVERAL HUMAN MONOCLONAL RHEUMATOID FACTORS

| Region: | FR-2 | CDR-2 | | | | | | | FR-3 | | | |
|---|---|---|---|---|---|---|---|---|---|---|---|---|
| Residue: | 49 | 50 | 51 | 52 | 53 | 54 | 55 | 56 | 57 | 58 | 59 | 60 | 61 |
| IgM-RF | Public Idiotype | | | | | | | | | | | | |
| 1. Sie | Wa | Tyr | Gly | Ala | Ser | Ser | Arg | Ala | Thr | Gly | Ile | Pro | Asp | Arg |
| 2. Wol | Wa | — | — | — | — | — | — | — | — | — | — | — | — | — |
| 3. Pom | Po | — | — | — | — | Thr | — | — | — | — | — | —Ala— | — |
| 4. Lay | Po | — | — | — | — | Thr | —Glu | Ala | — | — | —Val— | —Ser— | — |

IgM-RF : Boc Flo Gal Lew She Pom | Boc Flo Gal Lew She Pom

First
Antibodies:   Anti-PPH2  |  Anti-PPH3

Second
Antibodies:   Anti-PSH3  |  Anti-PWH3

FIG. 11

IgM-RF:

Anti-PWH2

IgM-RF: Cur Gar Glo Got Neu Pal Pay Pom Sle

Anti-PSH3
FIG. 10

IgM-RF: Cur Gar Glo Got Neu Pay Pom Sle Wol

Anti-PWH3
FIG. 13

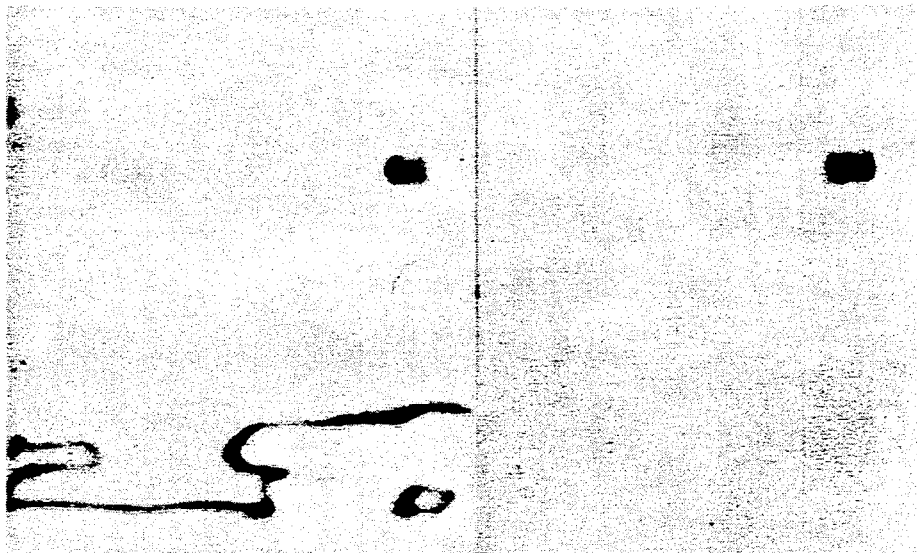
FIG. 14
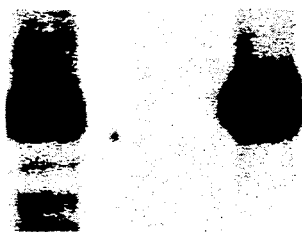
SIE
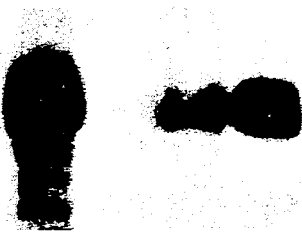
POM
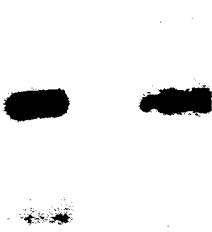
WOL
FIG. 16

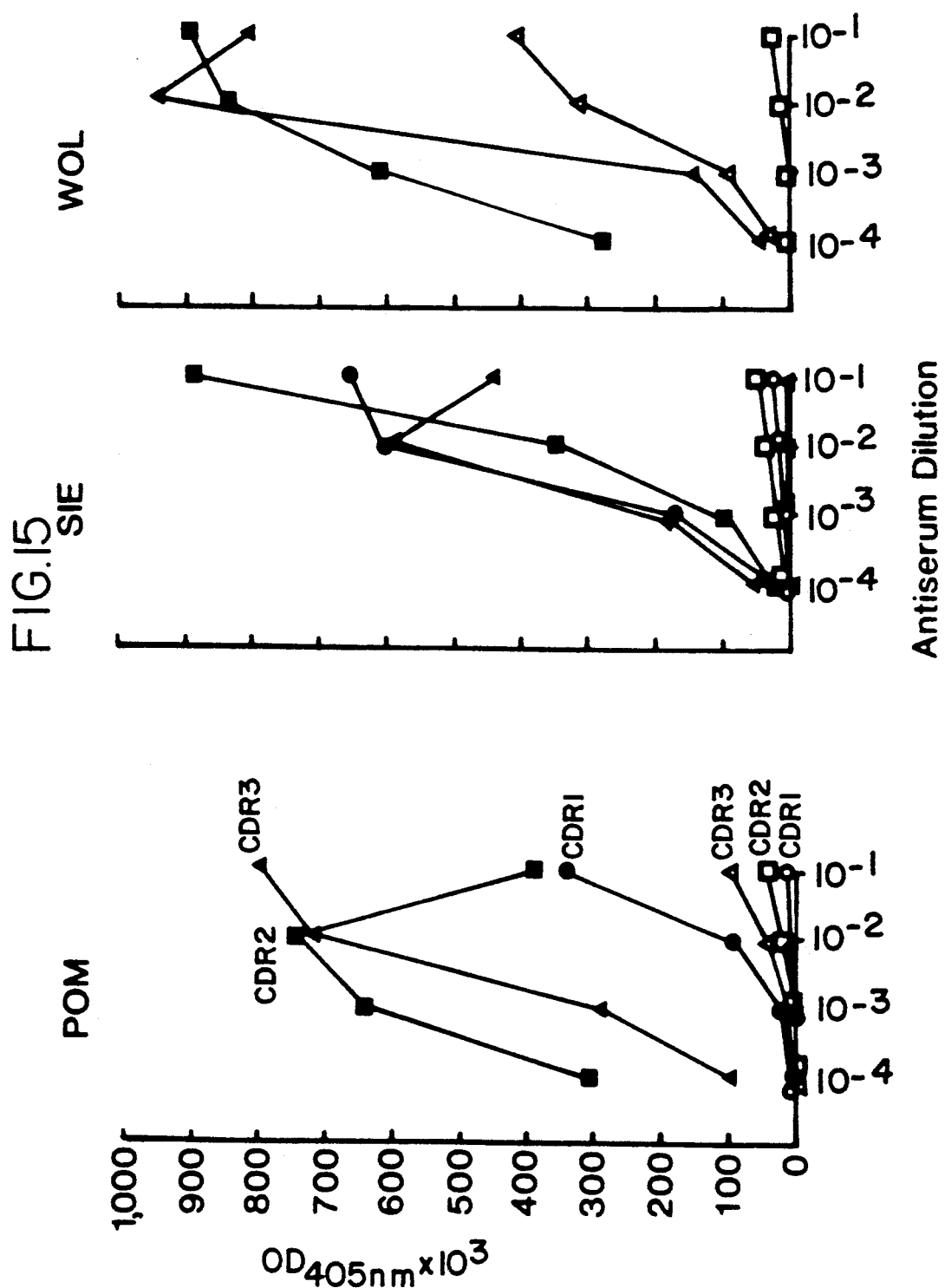

ANTI-IDIOTYPE ANTIBODIES INDUCED BY SYNTHETIC POLYPEPTIDES

This invention was made with the support of the Government of the United States, and the Government of the United States has certain rights in the invention.

CROSS-REFERENCE TO A RELATED APPLICATION

This is a continuation-in-part of copending application Ser. No. 566,172, abandoned filed on Dec. 28, 1983.

TECHNICAL FIELD

The present invention relates to chemically synthesized polypeptides having amino acid residue sequences that substantially immunologically correspond to the primary amino acid residue sequences of particular variable or hypervariable regions of immunoglobulins, and that, when administered either alone, as polymers or as conjugates bound to an antigenic carrier, induce the production of anti-idiotypic antibodies of predetermined specificities.

BACKGROUND

An antibody is an immunoglobulin molecule that has a specific amino acid residue sequence and thus binds only with the antigen that induced its synthesis (its immunogen) or with a closely related antigen (or immunogen). Immunoglobulin molecules include two kinds of polypeptide chains.

Each molecule consists of larger identical polypeptide chains referred to as heavy chains (H chains) and two identical smaller chains referred to as light chains (L chains). These polypeptide chains are held together by disulfide bonds and by noncovalent bonds, which are primarily hydrophobic. The heavy and light polypeptide chains are synthesized in vivo on separate ribosomes, assembled in the cell, and are secreted as an intact immunoglobulin molecule.

The understanding of the structure and function of immunoglobulins has been facilitated by studies of fragments produced by enzymatic cleavage of the antibody molecule. For example, treatment of an antibody molecule with the enzyme papain produces two antigen-binding fragments (designated "Fab") and a complement-binding fragment (designated "Fc"), which contains no antigen-binding capability but determines important biological characteristics of the intact immunoglobulin molecule. Treatment of an antibody molecule with the enzyme pepsin, on the other hand, produces a single antigen-binding fragment [designated "F(ab')$_2$"] and a complement-binding fragment (also designated "Fc") that is somewhat smaller than the Fc fragment produced by papain.

The constant region of H chains permits the differentiation of immunoglobulins into classes and subclasses, and confers certain biological properties such as the ability to activate complement, to cross the placenta, and to bind to polymorphonuclear leukocytes or macrophages.

In particular, five immunoglobulin classes (IgG, IgA, IgM, IgD, and IgE) are recognized on the basis of structural differences of their heavy chains including the amino acid residue sequence and length of the polypeptide chain. The antigenic determinants on the heavy chains also permit the identification and quantitation of the immunoglobulin classes by immunochemical assay techniques.

The amino-terminal one-half of the light chains and the amino-terminal one-quarter of the heavy chains of an immunoglobulin molecule vary in their amino acid residue sequence and are termed the variable regions (V regions) of the polypeptide chains. Portions of the V region of one heavy and of one light polypeptide chain constitute the site for antigen binding. A considerable variation in the amino acid residue sequence of the variable region of an immunoglobulin molecule can exist which produces the many different antibody specificities. A region of extreme variability in the primary sequence within a variable region is called a hypervariable region. [Capra et al., *Proc. Natl. Acad. Sci. USA*, 71, 845 (1974).]

Hypervariable regions contain residues that contact the antigen and bind to it on the basis of mutual complementarity (complementarity-determining region or CDR). The regions are discontinuous at the level of primary structure but converge at the level of tertiary structure to form the continuous, highly contorted sequence of the binding site.

The specificity of the molecular binding site of an antibody is termed its idiotype. The term idiotype denotes the unique variable (V) region sequences produced by each type of antibody-forming cell. An antibody having a binding site specificity for the binding site of another antibody is termed an anti-idiotypic antibody.

The same amino acid sequence variation that produces the antigen binding specificity of an immunoglobulin also determines which idiotypic determinants are present. Thus, particular idiotypes are almost invariably associated with immunoglobulins of a particular specificity. As such, idiotypes can serve as antigenic markers for immunoglobulins with a particular specificity and, by virtue of their surface immunoglobulin, B lymphocytes of the same specificity.

The terms "cross-reactive" and "cross-reactivity" refer to the ability of an antibody to bind antigens other than its idio-specific antigen. Cross-reactive anti-idiotypic antibodies can be divided into two major groups.

One group comprises those anti-idiotypic antibodies that recognize idiotypic antigenic determinants that are associated with specific amino acid residue sequences in the heavy and light chain variable regions. Anti-idiotype antibodies of this group often reflect the action of inherited immunoglobulin structural genes. Consequently, these antibodies do not cross-react in subjects that are not genetically similar.

The second group includes anti-idiotypic antibodies that are cross-reactive to the internal image of the antigen. This type of anti-idiotypic antibody is elicited by immunization with an intact immunoglobulin and usually recognizes idiotypic antigenic determinants as a result of a particular quaternary interaction of the light and heavy chains. The antigenic site recognized by this group of anti-idiotypic antibodies, however, is not associated with a particular light or heavy chain amino acid residue sequence.

Because the antibody binding site bears the internal image of the antigen; i.e., mimics the size, shape, charge and/or van der Waals attraction of the antigen, the second group of anti-idiotypic antibody binds to many different antibodies of the same specificity. The idiotypes recognized by such antibodies can be produced by individuals with different genetic backgrounds and are controlled by genes that bear no special relationship.

Anti-idiotype immunotherapy can be very useful in the treatment of autoimmune disease, by neutralizing pathological auto-antibodies. Anti-idiotypic therapy can be highly specific. But such therapy suffers from the disadvantages associated with passive administration since the anti-idiotypic antibodies must be produced in a non-human species. Therefore, a significant possibility exists that an individual so treated will develop an immune response against the passively administered antibodies, which response can negate any potential therapeutic effect. This is particularly true because the antibodies must be administered many times to produce the desired result.

Moreover, all anti-idiotypic antibodies have previously been generated by immunizing the host with the target immunoglobulin. The resulting polyclonal antisera must then be extensively purified to produce antibodies having the desired anti-idiotypic specificity. The selected, purified, "monoclonal" antibodies must then be carefully tested to determine their specificities.

The structural correlates of idiotypes have been sought in several well-defined antibody systems. See Kunkel et al., *Science*, 140, 1218 (1963); Capra et al., *Proc. Natl. Acad. Sci. USA*, 71, 4032 (1974); Weigert et al., *J. Exp. Med.*, 139, 137 (1974); Klapper et al., *Ann. Immunol. (Inst. Pasteur)*, 127C, 261 (1976); Schilling et al., *Nature*, 283, 35 (1980); Capra et al., *Immunol. Today*, 3, 332 (1982); and Capra et al., *Immunol. Today*, 4, 177 (1983). These studies suggest that a hypervariable region (containing a complementarity-determining region or a CDR) of an immunoglobulin is the structural correlate of an idiotypic determinant.

In particular, in the murine anti-dextran system, one private (or individual) idiotype and one public (or cross-reactive) idiotype were assigned to the third and second hypervariable regions, respectively, of the heavy chain. Schilling et al., supra. However, in most systems, it has proven extremely difficult to associate a particular idiotypic determinant with a specific amino acid residue sequence (Capra et al., *Immunol. Today*, 4, supra.) Rather, anti-idiotypic antibodies elicited by immunization with an intact immunoglobulin usually recognize determinants dependent upon a particular quaternary interaction or "internal image" of both of the light and heavy chains. (Capra et al., *Id.*)

Lerner et al. have been successful in obtaining protection of animals by the use of vaccines against pathogens that utilize synthetic polypeptides having amino acid residue sequences of short to moderate length as immunogens. See Sutcliffe et al., *Science*, 219, 660 (1983). Such synthetic polypeptides induce antibodies specific for predefined determinants of intact proteins.

As described herein, synthetic polypeptide technology can avoid the previously described difficulties associated with conventional anti-idiotypic therapy. According to the present invention, described in detail hereinafter, polypeptides having relatively short amino acid residue sequences that substantially correspond to the portion of the immunoglobulin primary sequence that forms the idiotype can be synthesized, coupled to an appropriate carrier and inoculated into animal hosts, including humans, as immunogens to raise antibodies. The resulting antisera recognize the synthetic polypeptide having an amino acid residue which immunologically corresponds substantially to a primary amino acid residue sequence of a portion of an immunoglobulin variable region, including an idiotypic antigenic determinant. The antisera are therefore idiotype specific. Such antisera produced by synthetic polypeptides are thus of predetermined specificity and the necessity for extensive purification and specificity testing is eliminated substantially.

Briefly, the polypeptide alone is not immunogenic in most cases. Small molecules such as the peptides of this invention, can be coupled to appropriate antigenic carriers to form conjugates. The resulting peptide-carrier conjugate is immunogenic. Antibodies are produced to both the peptide antigen and antigens of the carrier. However, anti-carrier antibodies so produced do not interfere with the specificity of diagnostic assays, effective immunoregulation or any use contemplated by the invention.

In addition, such synthetic polypeptides alone, as conjugates or as polymers can be administered to individuals to raise antibodies that immunoreact with the particular idiotypes of that individual. Autologous anti-idiotypic antibodies are well documented and are widely believed to be very important in immunoregulation. One advantage in the use of synthetic polypeptide-containing antigens (immunogens) is that antibodies reactive with otherwise non-immunogenic determinants can be elicited. Therefore, appropriate synthetic polypeptides can induce anti-idiotypic antibodies in an individual that are directed against a particular idiotype of that individual whereas this could not be achieved by immunizing with the intact immunoglobulin which results in antibodies against substantially all the antigenic determinants of the immunoglobulin.

Thus, an individual can be actively immunized against a pathological idiotype and the number of therapeutic interventions required can be substantially reduced compared to conventional immunization with an intact immunoglobulin. Also, the possibility of an immune response against the anti-idiotypic antibodies can be reduced substantially as compared to antibodies produced in another animal species and passively administered to a human.

Polypeptides can also be synthesized to mimic an antigen under attack by pathological auto-antibodies. These polypeptides can block or inhibit the interaction between the antigen and the undesirable auto-antibodies, thereby significantly impeding the disease process.

It is believed that certain idiotypes occur very frequently in particular syndromes. Synthetic polypeptides, corresponding to such idiotypes can be used to elicit antibodies of predetermined specificity for such syndromes, and can then be applied in the diagnosis and treatment of that syndrome.

BRIEF SUMMARY OF THE INVENTION

The present invention contemplates a synthetic polypeptide having an amino acid residue sequence containing about 6 to about 40 amino acid residues and preferably about 8 to about 20 amino acid residues, that substantially immunologically corresponds to a primary amino acid residue sequence of an idiotypic antigenic determinant of an immunoglobulin. When injected into a host in an effective amount and in a physiologically tolerable vehicle, the synthetic polypeptide has the capacity either alone, as a polymer or as a conjugate of the polypeptide bound to a carrier, of inducing the production of antibodies to the antigenic determinant of the immunoglobulin.

The invention also contemplates an inoculum comprising an effective amount of a synthetic polypeptide having an amino acid residue sequence containing about 6 to about 40 amino acid residues that substantially immunologically corresponds to a primary amino acid residue sequence of an idiotypic antigenic determinant of an immunoglobulin in a physiologically tolerable vehicle.

The invention further contemplates antibodies raised in an animal host to a synthetic polypeptide of this invention.

In another aspect the invention contemplates a diagnostic system for assaying for the presence of an antigenic determinant of an immunoglobulin including in at least one container an effective amount of the antibodies of this invention.

In yet another aspect the invention contemplates a method of producing an anti-idiotype antibody comprising administering to a host mammal a synthetic polypeptide of this invention in an amount sufficient to induce the production of antibodies and maintaining said host mammal for a period of time sufficient to produce the antibodies.

The invention also contemplates a method of immunoregulating a human immune system comprising the following steps: (a) providing an inoculum comprising an effective amount of a synthetic polypeptide of this invention is a physiologically tolerable vehicle, and (b) introducing the inoculum into the human to interact with the immune system of the human.

The invention further contemplates a method for assaying for the presence of an idiotypic antigenic determinant of an immunoglobulin in a sample comprising the following steps: (a) providing an antibody induced by a polypeptide of this invention that substantially corresponds immunologically to the antigenic determinant; (b) admixing a predetermined amount of the antibody with a predetermined amount of the sample to be assayed to form an admixture; (c) maintaining the admixture for a period of time sufficient for the antibody to immunoreact with and to bind to idiotypic antigenic determinants that may be present in the admixture; and (d) determining the amount of binding between the antibody and the determinant of the immunoglobulin.

The present invention contemplates synthetic polypeptides that mimic idiotypic antigenic determinants on human rheumatoid factor molecules and elicit the production of antibodies (anti-idiotypic antibodies) of predetermined specificity that are reactive with those idiotypes. Such antibodies can be useful in the treatment of autoimmune disease and certain diseases of B-lymphocytes. Such antibodies can also be used in the diagnosis of disease where a particular idiotype occurs.

An "anti-antibody" or "anti-idiotypic antibody" induced by a peptide of this invention has a predetermined specificity and has a binding site having substantially the same configuration as the primary sequence of the variable or hypervariable region of the immunoglobulin. Antibodies of this type provide an improved means for defining the structure of idiotypes, as well as providing means for diagnostics and therapy.

The method of the present invention produces antibodies against an idiotypic antigenic determinant of a naturally occuring protein and can result, depending on the CDR utilized, in a large fraction of the elicited sera being reactive against the natural and the denatured protein. Specifically, antibodies raised against the second and third CDR of the light chain of IgM-RFs are cross-reactive anti-idiotype antibodies that react with intact and denatured parent protein and the majority of human monoclonal IgM-RFs studied, as described in detail hereinafter. Antisera raised against synthetic peptides corresponding to the third heavy chain CDR consistently recognize idiotypes expressed by intact IgM-RF autoantibodies. In contrast, high titer antibodies against synthetic peptides representing the first and second heavy chain CDR infrequently bind to the intact IgM-RF molecule.

It remains unclear whether in a given anti-polypeptide serum the same antibody molecules are responsible for the interaction with both native and denatured proteins or whether different antibody molecules in the antiserum react preferentially with one or the other of the two protein states. Another aspect of this invention is that the method of producing antibodies against synthetic polypeptides can be used to raise antibodies against idiotypic antigenic determinants that are not naturally immunogenic in the host. That is, certain portions of a macromolecule have the ability to be bound by an antibody (i.e., are antigenic) but do not elicit the production of antibodies (i.e., are not immunogenic). Certain idiotopes are an example of such determinants that are antigenic but not immunogenic. Thus, the polypeptides of the present invention can be used to terminate tolerance and thereby target the immune response to restricted regions of self-proteins.

Anti-idiotype antibodies produced according to this invention have several distinct advantages over anti-idiotypic antibodies produced by conventional immunization with an intact immunoglobulin.

Conventional anti-idiotypic sera distinguish the idiotype on the basis of the quarternary structure of the immunoglobulin. That is, the anti-idiotypic antibody recognizes a three dimensional protein structure created by the folding of the primary sequence and the juxtalocation of non-contiguous regions of the primary sequence.

Anti-idiotype antibodies produced according to this invention can distinguish idiotopes on the basis of continuous, sequence-defined determinants; i.e., the idiotypic antigenic determinant. The recognition site does not require the juxtalocation of non-contiguous regions of the primary sequence. This results in an ability to generate anti-idiotypic antibodies with a high degree of specificity to a predetermined region of the primary sequence. This was not possible with conventional methodology.

Another advancement of this invention over conventional methodology is that anti-idiotypic antibodies can be produced against a particular idiotype without the need for substantial antibody purification. Conventional techniques for raising anti-idiotypic antibodies involve immunizing a host with the appropriate immunoglobulin or a fragment thereof. This results in a polyclonal response against the various idiotypic antigenic determinants on the immunoglobulin. The sera must then be passed over an adsorption column to separate and to isolate the particular anti-idiotope of interest, and to produce serum with specificity for an idiotype.

In contrast, the present invention requires no adsorption purification. By the method of this invention, highly specific anti-idiotypic antibodies are produced against a predetermined and predefined idiotype.

Still further, synthetic polypeptide technology provides new analytical tools that can play a paramount role in answering questions about the structural correlates of idiotype. Anti-polypeptide antisera directed against certain idiotypic determinants located in the antigen binding regions of antibodies can be a way to relate protein structure to antigen binding. For example, one can induce a set of antibodies to different regions in the vicinity of the binding site and determine which perturb antigen-antibody union.

BRIEF DESCRIPTION OF THE DRAWINGS

In the drawings, which constitute a portion of this disclosure.

Antibody binding was inhibited by: polypeptide (●), IgM-RF (Sie;■) and control polypeptide (▲), at the indicated concentrations in units of micrograms per milliliter (ug/ml). The ordinate for each graph is percent binding relative to the highest binding achieved in the assay as 100 percent. The abscissa for each graph is the concentration of peptide or RF (Sie) in ug/ml.

Figure 2:
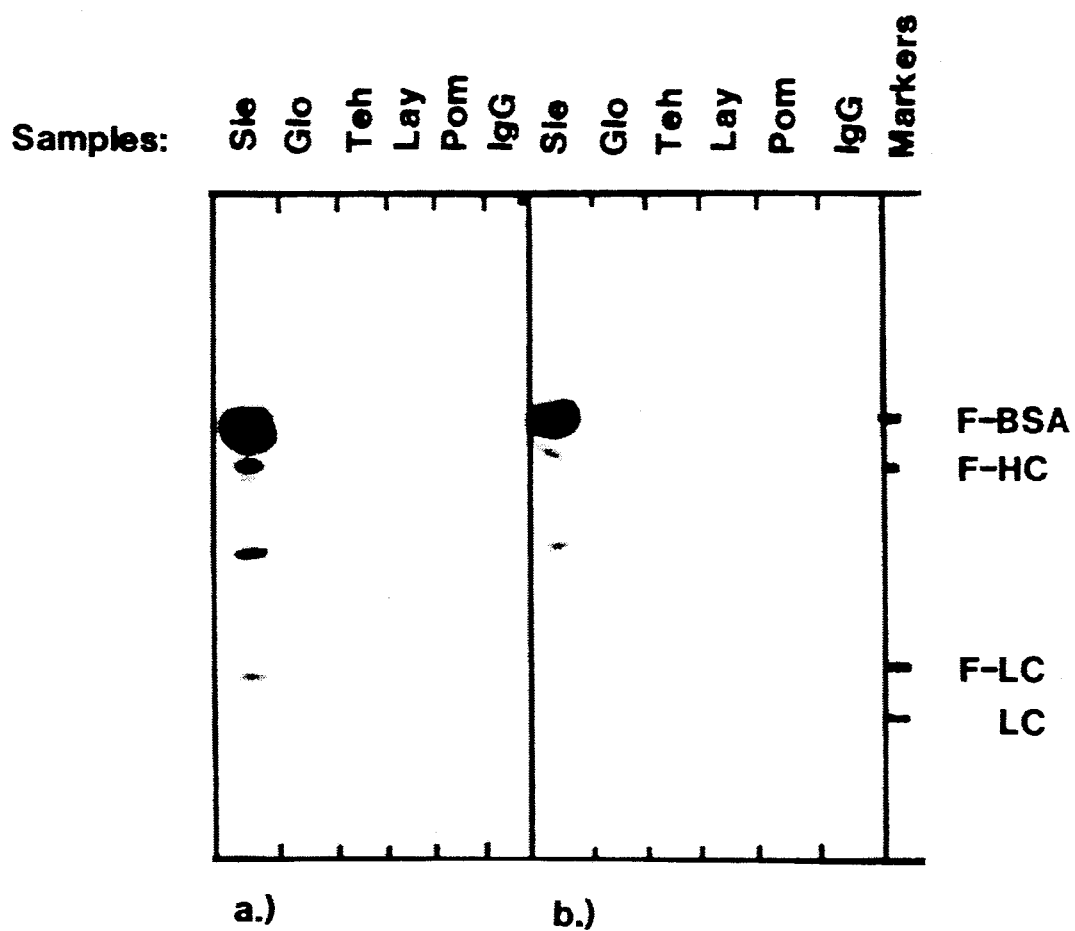

FIG. 2 is a photograph of a Western blot of 5 monoclonal human rheumatoid factors and pooled human IgG, developed with separate synthetic polypeptide-induced anti-idiotypic antisera from two immune rabbits (panels a and b). Each antibody identifies primarily a band of about 70,000 daltons which corresponds to the heavy chain of IgM-RF (Sie). Control studies with a polyvalent anti-heavy chain antibodies indicated that the minor bands of lower molecular weight represented minor proteolytic degradation products of the heavy chain. The markers used are: fluoresceinated-bovine serum albumin (F-BSA; 68k), fluoresceinated-gamma H chain (F-HC; 53k), fluoresceinated L chain (F-LC; 28k) and L chain (25k).

FIG. 3 identifies the amino acid residue sequences of idiotypic antigenic determinants (corresponding to polypeptide PSL2) of certain reported rheumatoid factors. The regions and residue numbers are as assigned by Kabat et al., "Sequence of Proteins of Immunological Interest", U.S. Department of Health and Human Services (1983). The public or cross-reactive idiotypes have been reported by Kunkel et al., *J. Exp. Med.*, 137, 331 (1973). The amino acid residue sequences for IgM-RF (Sie) and IgM-RF (Wol) have been reported by Andrews et al., *Proc. Natl. Acad. Sci. USA*, 78, 3799 (1981), whereas the amino acid residue sequences for IgM-RF (Pom) and IgM-RF (Lay) have been reported by Klapper et al., *Ann. Immunol.* (Inst. Pasteur), 127C, 261 (1976). Only residues different from those in Sie are illustrated. CDR-2 represents the second complementarity determining region, while FR2 and FR3 represent the second and third framework regions.

Figure 4:
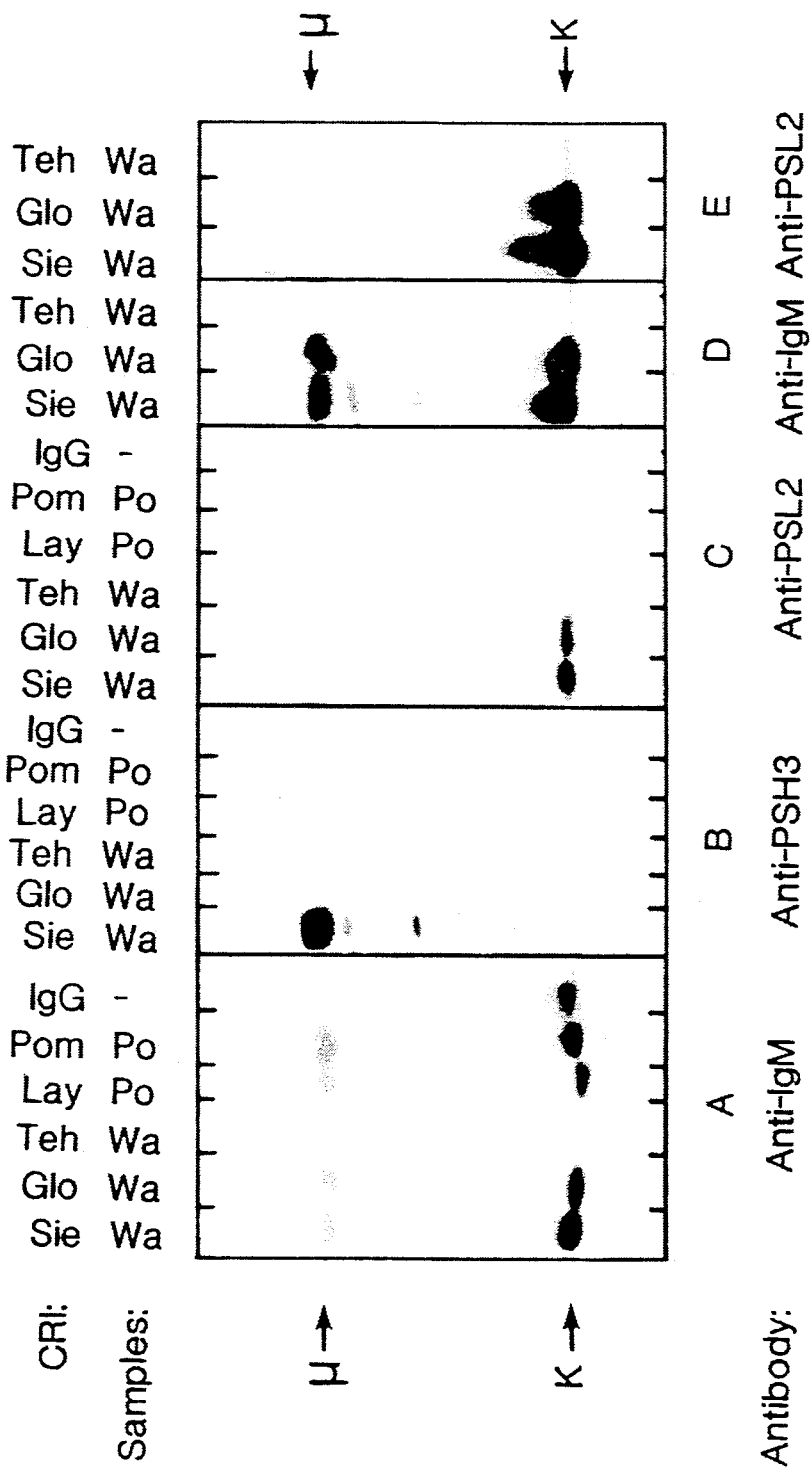

FIG. 4 is a photograph of a Western blot analysis of the antibody activity of the anti-PSL2 antiserum. About 20 micrograms of each indicated sample were loaded on each gel. After electrophoresis on sodium dodecyl sulfate-polyacrylamide gel and electrophretical transfer to nitrocellulose paper, the samples were reacted respectively with anti-IgM (A, D), anti-PSH3 (B) and anti-PSL2 (C, E) antisera. After subsequent development with the $^{125}$I-protein A (*Staphylococcus aureus*), the papers were finally exposed to film overnight, except that (D) and (E) were exposed for three days. The Greek letters mu and kappa and their accompanying arrows indicate the positions of the mu and kappa chains, respectively.

Figure 5:
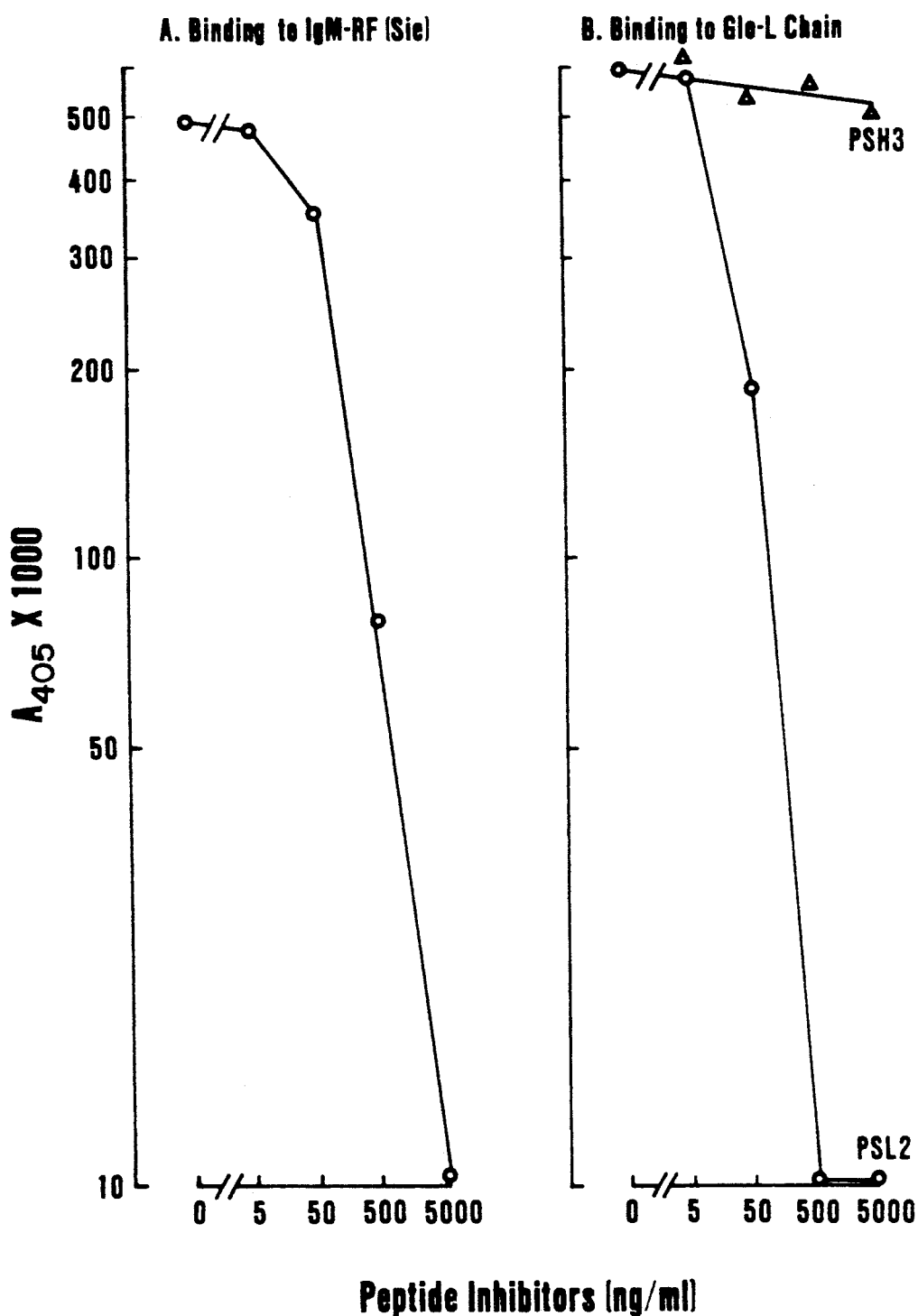

FIG. 5 contains two graphs that illustrate that synthetic polypeptide PSL2 inhibits the binding of PSL2-induced antibodies to the IgM-RF (Sie) (panel A); and to the isolated light chains of RF-Glo (●; panel B). In addition, inhibition by the control synthetic PSH3 (▲) is shown in panel B. The ordinates are in units of absorbance at 405 nanometers (nm). The abscissas are in nanograms (ng) per milliliter (ml).

Figure 6:
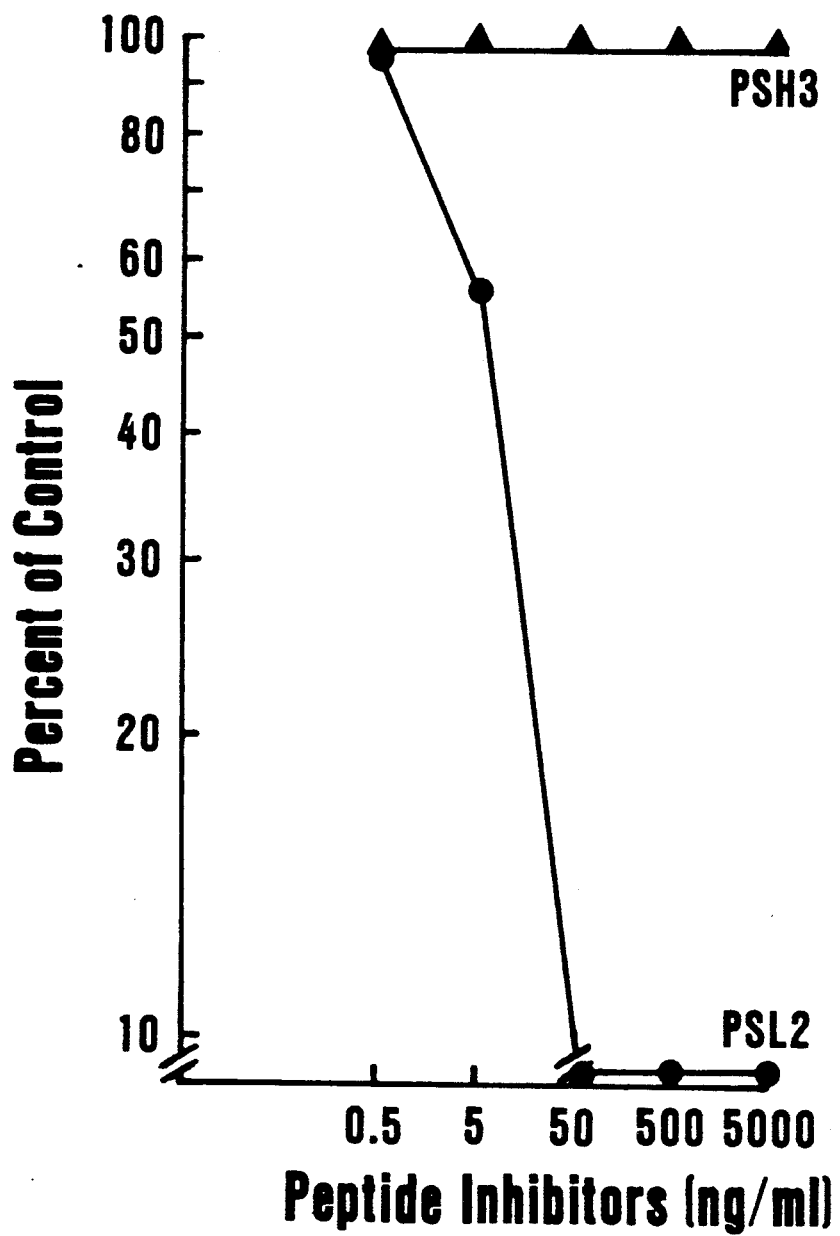

FIG. 6 is a graph that illustrates inhibition of the IgM-RF Sie binding to the bound synthetic polypeptide-induced anti-idiotypic antibody. The synthetic polypeptide PSL2 (●) and the control synthetic PSH3 (▲) were added at the indicated concentrations to wells precoated with affinity-purified anti-PSL2 antibodies. After incubation for one hour at room temperature (23° C.), alkaline phosphatase linked IgM-RF (AP-IgM-RF) Sie (10 micrograms per milliliter) was added to each well and the plate was incubated for another 1.5 hours at room temperature. Thereafter, the plate was washed, and the absorbance at 405 nanometers was measured one hour after the addition of substrate to the wells. The ordinates and abscissas are as in FIG. 5.

Figure 7:
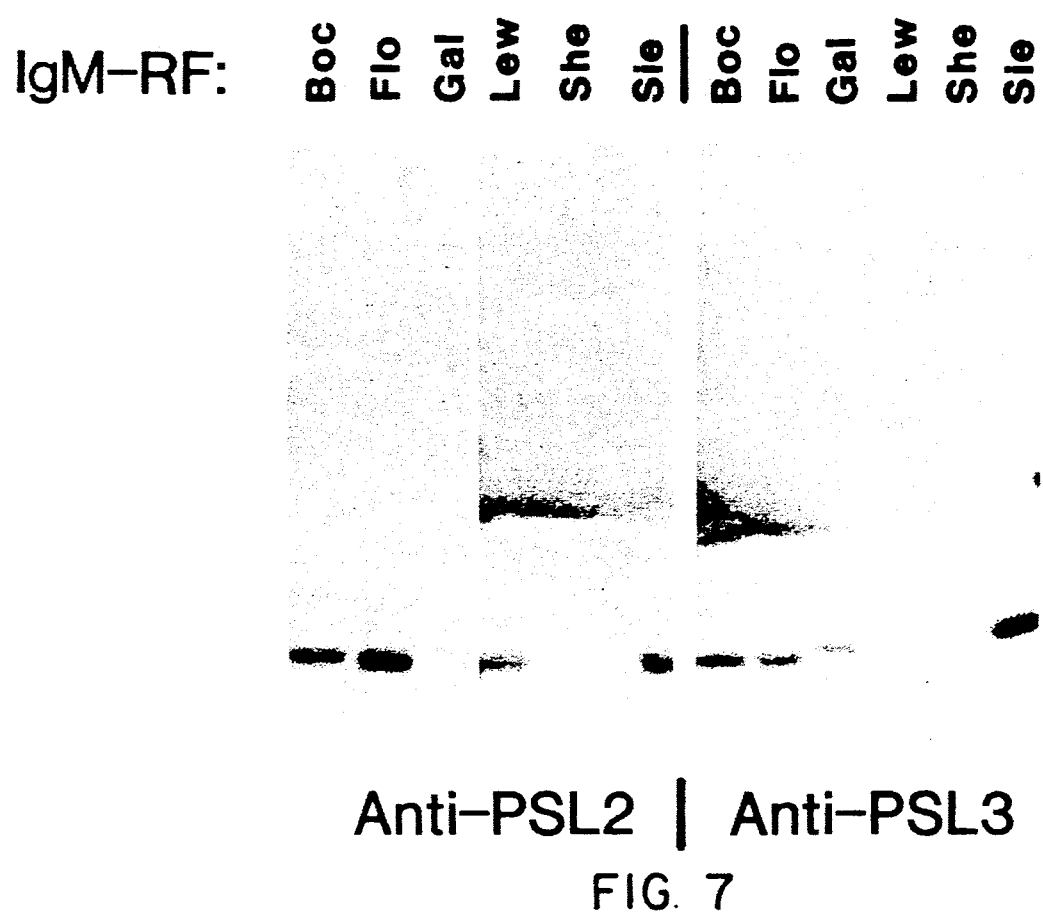

FIG. 7 is a photograph of an immunoblot analysis of the anti-PSL2 (at 1:500 dilution) and anti-PSL3 (at 1:50 dilution) antisera. About 20 micrograms (ug) of each IgM-RF paraprotein was used in each lane. After electrophoresis and transfer of samples, the papers were reacted with the indicated antisera, developed with radio-labeled protein A and finally exposed to XAR film overnight.

Figure 8:
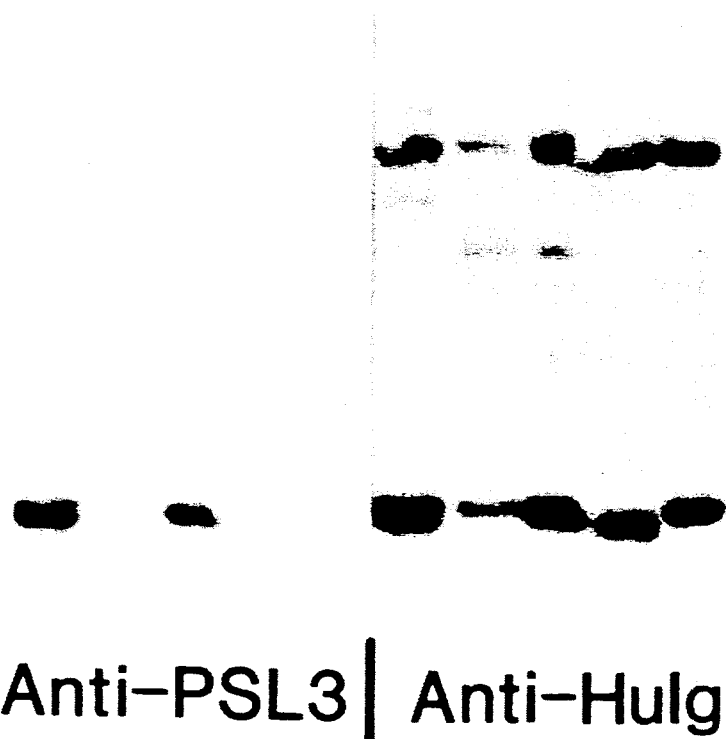

FIG. 8 is a photograph of an immunoblot analysis of RFs bearing either the Wa cross-reactive idiotope (Wa-CRI) or the Po cross-reactive idiotope (Po-CRI). The procedure was performed as described in FIG. 7, except that only 8 $\mu$g of IgM-RF Wol was loaded, and that polyspecific rabbit anti-human Ig antibodies (anti-HuIg) (IgG fraction, at 5 $\mu$g/ml) were used to show the relative amount of IgM-RF blotted onto nitrocellulose paper.

Figure 9:
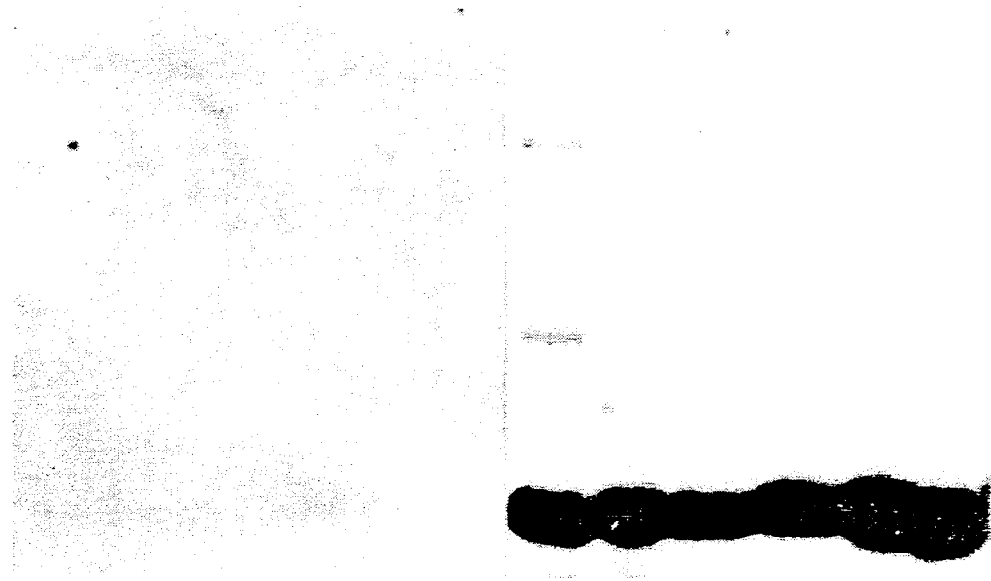

FIG. 9 is a photograph of an immunoblot analysis of six Bence Jones kappa light chain proteins (K Light chains). The same procedure was followed as in FIG. 8.

FIG. 10 is a photograph of an immunoblot analysis of the anti-PSH3 antiserum with paraproteins as indicated. The same procedure was followed as in FIG. 7.

FIG. 11 is a photograph of an immunoblot analysis of six IgM-RFs with four different synthetic peptide-induced anti-idiotypic antisera. The procedures were performed as in FIG. 7, except that the papers were reacted first with either anti-PPH2 (panel a) or anti-PPH3 (panel b), and then with either anti-PSH3 (panel c) or anti-PWH3 (panel d) respectively.

Figure 12:

FIG. 12 is a photograph of an immunoblot analysis of 14 IgM-RFs with the anti-PWH2 antiserum. The same procedure was followed as in FIG. 7.

FIG. 13 is a photograph of an immunoblot analysis of nine IgM-RFs with the anti-PWH3 antiserum. The same procedure was followed as in FIG. 7.

FIG. 14 is a photograph of an immunoblot analysis of nine IgM-RFs with the indicated antisera. The same procedure was followed as in FIG. 7.

FIG. 15 is a series of three graphs illustrating reactivity of anti-peptide antibodies with the immunizing peptides as determined by ELISA. Plates were precoated with 10 $\mu$g/ml of each peptide as solid support-affixed antigens, and reacted with increasing dilutions of corresponding antisera, followed by alkaline phosphatase-labeled goat anti-rabbit antibody. The closed symbols represent binding of antisera to immunizing peptide (●-CDR1■-CDR2,▲-CDR3) and the open symbols represent binding to the irrelevant peptide PWL3 (o -CDR1, □- CDR2, Δ- CDR3). Binding is expressed as absorbance values at 405 nm×10³ at a time period 30 minutes following the addition of substrate. Points represent the mean of duplicate determinations, with less than 5% variability between replicates. Ordinates are as in FIG. 5, while the abscissas are dilutions of antisera.

FIG. 16 is a series of three photographs of immunoblot analyses of reactivity of anti-peptide antibodies with isolated RF heavy chains. All anti-peptide antisera were diluted 1:20. Binding was assessed by binding of ¹²⁵I-protein A followed by autoradiography.

Figure 17:
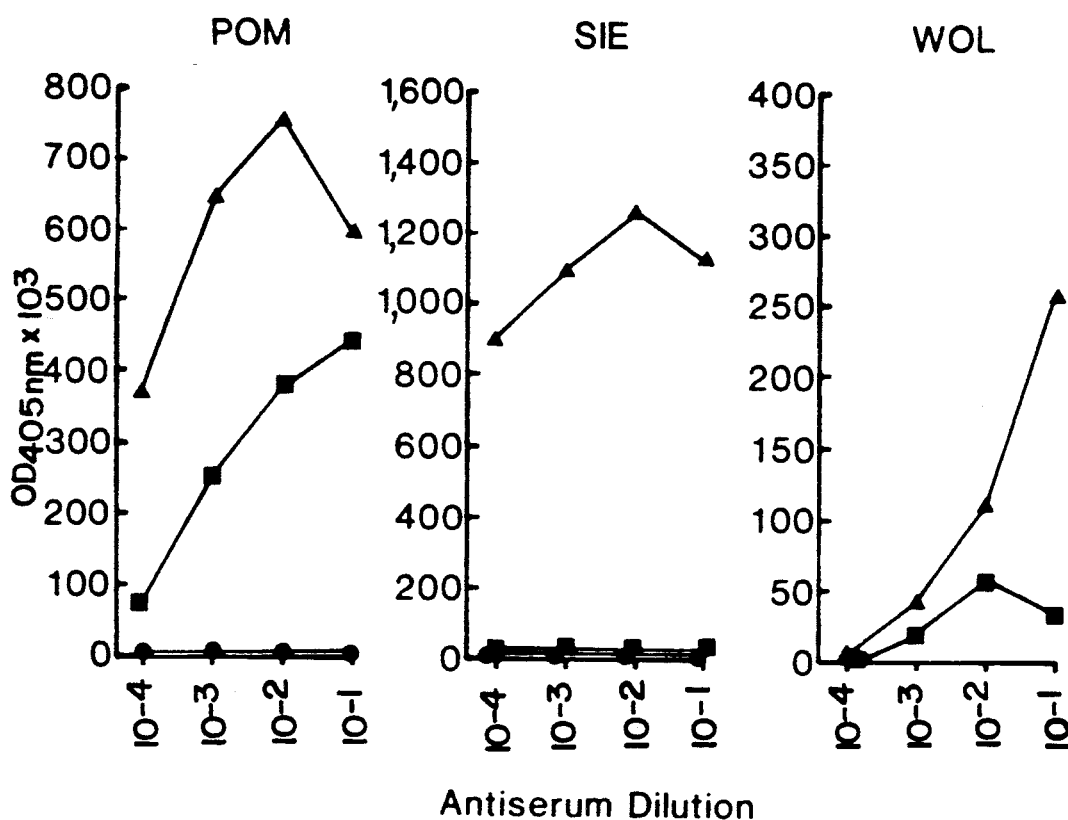

FIG. 17 is a series of three graphs illustrating reactivity of anti-peptide antibodies with intact IgM-RF as determined by ELISA. Plates were coated with 2 μg/ml (Pom, Sie) or 10 ug/ml (Wol) and reacted with serial dilutions of antisera, followed by alkaline phosphatase-labeled goat anti-rabbit antibody (●-CDR1,■-CDR2,▲-CDR3). The values represent the difference in absorbance values at 405 nm×10³ dilutions at 60 minutes following the addition of substrate. Abscissas and ordinates are as in FIG. 15.

Figure 18:

FIG. 18 is a photograph of an immunoblot analysis of the indicated antisera illustrating the epibody activity of anti-PGL1 antiserum. The same procedure was followed as in FIG. 7. 10 ug of each sample was loaded into each slot. Anti-PGL1 was used at 1:20 dilution, while anti-human Ig (anti-Ig) was used at 5 ug/ml, and inhibitor PGL1 at 50 μg/ml.

Figure 19:
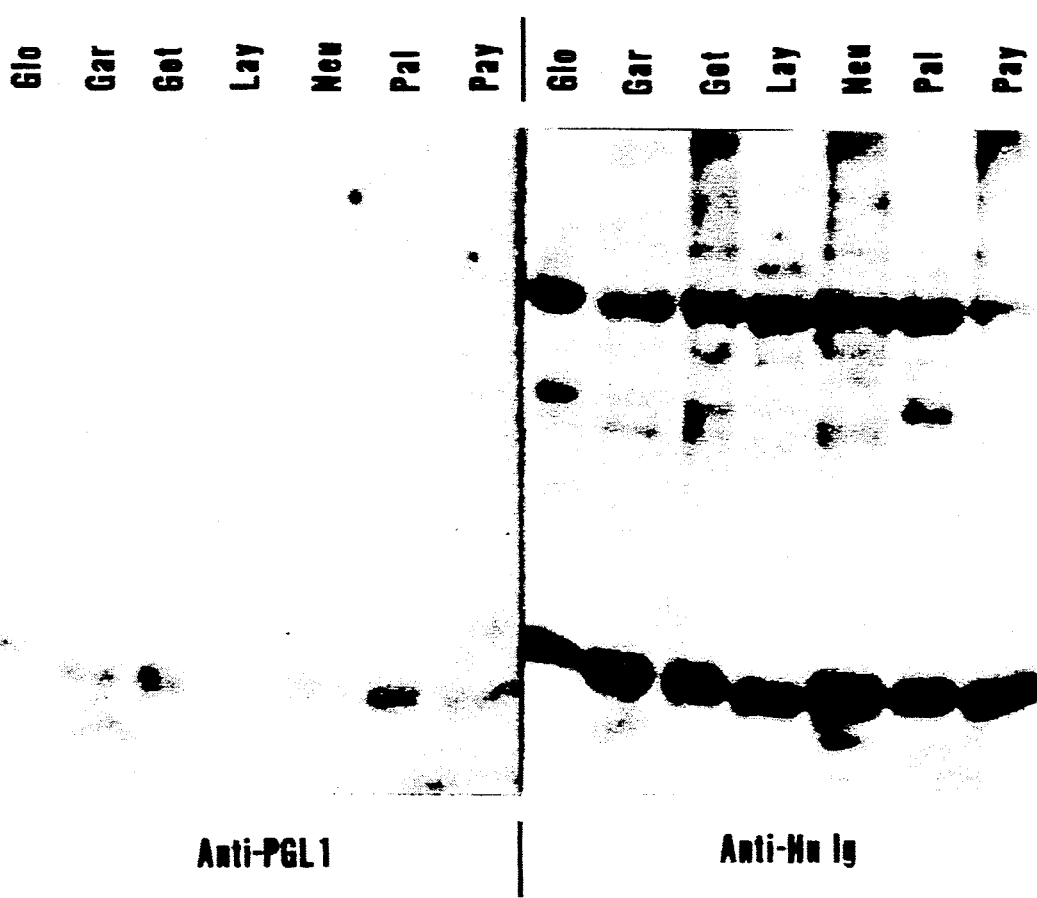

FIG. 19 is a photograph of an immunoblot analysis of the indicated antisera illustrating the fine specificity of anti-PGL1 antisera. The indicated seven human monoclonal IgM-RFs were used at 10 ug/slot and were reacted with the anti-PGL1 antiserum at 1:20 dilution or anti-human Ig antiserum at 5 ug/ml. The same procedure was followed as in FIG. 7.

Figure 20:
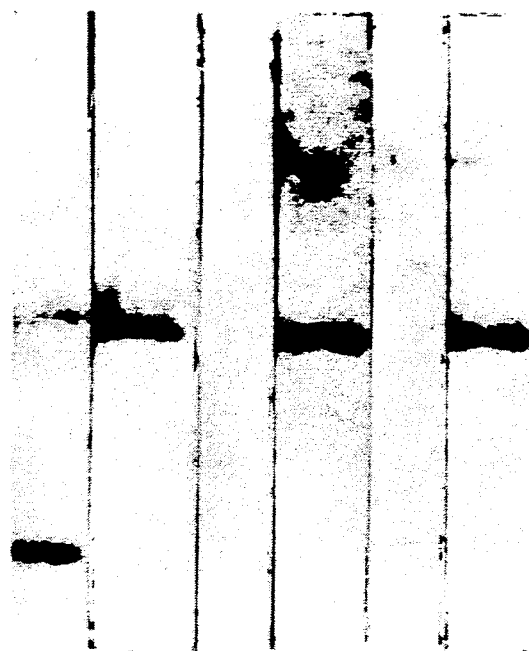

FIG. 20 is a photograph of an immunoblot analysis of human IgG affinity isolated anti-PGL1 antibodies. The same procedure was followed as in FIG. 7. Nitrocellulose paper with polypeptides (either human IgG or IgM-RF Glo) were incubated with antibodies [human IgG (HuIgG) eluate of anti-PGL1]and the indicated amount of inhibitor PGL1. The analysis shows that the antibodies consisted of two sets: antibodies with epibody activity and

DETAILED DESCRIPTION

I. Introduction

A. Definitions

Throughout the application, the terms "peptide" and "polypeptide" are used interchangeably. The terms "synthetic polypeptide" or "synthetic peptide" mean a chemically derived chain of amino acid residues linked together by peptide bonds that is free of naturally occurring proteins and fragments thereof. Such synthetic polypeptides can elicit production of anti-idiotypic antibodies in a host.

The phrase "immunologically corresponds substantially" in its various grammatical forms is used herein in relation to polypeptide sequences to mean the polypeptide sequence described or a polypeptide with substantially the same antigenicity that induces production of antibodies that bind to the polypeptide as well as to polypeptides having the same amino acid residue sequence as the idiotypic antigenic determinant.

The term "substantially corresponds" in its various grammatical forms is used herein in relation to polypeptide sequences to mean the polypeptide sequence described plus or minus up to three amino acid residues at either or both of the amino- and carboxy-termini and containing only conservative substitutions in particular amino acid residues along the polypeptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to mean those amino acid residues that normally either bear no charge or normally bear a charge, respectively, at physiological pH values. Exemplary nonionic residues include Thr and Gln, while exemplary ionic residues include Arg and Asp.

The word "antigen" has been used historically to mean the entity that is bound by an antibody as well as to mean the entity that induces the production of the antibody. More current usage limits the meaning of antigen to that entity bound by an antibody, while the word "immunogen" is used for the entity that induces antibody production. In some instances, the antigen and immunogen are the same entity as where a synthetic polypeptide is utilized to induce production of antibodies that bind to the polypeptide. However, the same polypeptide can be utilized to induce antibodies that also bind to a whole protein such as immunoglobulin, in which case the polypeptide is both immunogen and antigen, while the immunoglobulin is an antigen. Where an entity discussed herein is both immunogenic and antigenic, it will generally be termed an antigen.

An idiotypic antigenic determinant, as used herein, is the continuous, primary sequence-defined determinant in a variable region of an immunoglobulin molecule. The determinant includes at least a portion of a binding site or complementarity determining region and may include adjacent framework regions.

B. General Idiotypic determinants are generally believed to be involved in immunoregulation as described by Jerne, *Ann. Immonol. (Inst. Pasteur)*, 1255, 373 (1974) and Binion et al., *J. Exp. Med.*, 156, 860 (1982). Control of the system also appears to involve idiotype specific T-cells as described by Milburn et al., *J. Exp. Med.*, 155, 852 (1982). Evidence shows that the predominant expression of certain idiotypes may be the result of a regulatory process rather than a restricted immunological repertoire as described by Casenza et al., *Immunological Rev.*, 34, 3 (1977).

Since idiotype and anti-idiotypic antibodies are involved in immune regulation, it is possible to manipulate the immune response by inducing autologous anti-idiotypic antibodies as described in Casenza et al., supra. This manipulation with anti-idiotypic antibodies is believed to have considerable medical significance in certain B-cell malignancies and autoimmune diseases. In those autoimmune diseases where the injurious antibody is of restricted origin, it may be possible to use synthetic immunogens to modulate or even eliminate the B cell clones producing the antibody.

Such autologous anti-idiotypic antibodies useful in manipulating the immune response can be produced in an animal according to the method of the present invention. If a specific clonal type is sought to be regulated, then anti-idiotypic antibodies against a private idiotope should be raised. But, a private idiotope is an idiotope found on only one or a few clones of an antibody of a given specificity. If regulation of all antibodies of a given specificity is sought, then anti-idiotypic antibodies against a public or cross-reactive idiotope should be raised.

Anti-idiotype antibodies have a second mode of function to combat autoimmune diseases and transplant or graft regulations. For example, an anti-idiotypic antibody can block or obstruct an antibody binding site so as to preclude union between the injurious antibody and its antigen.

An "antigenic determinant" is a portion of the structural configuration of a macromolecule which has the capability to be bound by an antibody. Further explanation of an "antigenic determinant" is best accomplished by way of example. A simple protein is comprised of a linear chain of amino acid residues. This chain folds into a three dimensional structure. Certain portions of the chain are internal and other portions are external in relation to the environment of the protein. In addition, amino acid residues that are far apart in the primary sequence can be brought into close proximity by the folding. A protein structural arrangement (configuration) thereby results.

Certain portions of that configuration are such that they have the ability to be bound by an antibody of appropriate specifity; that is, they are antigenic determinants. These portions of the configuration can be thought of as having the right "shape", proper neighboring molecular environment, to bind an antibody. The antigenic determinants of particular interest in this invention are primary amino acid residue sequences located in the idiotypic region of an immunoglobulin and are therefore termed idiotypic antigenic determinants.

The presence of an antigenic determinant on a molecule is not limited to simple proteins. The ability is general to most natural macromolecules which include, for example, glycoproteins, dextrans, multipolypeptide chain proteins and the like.

Not all protein or other macromolecule antigenic determinants are immunogenic, as noted generally before. This is so for several reasons. First, the animal into which the determinant is introduced can have tolerance to the antigenic determinant. Second, the molecular environment around the determinant may not be right for eliciting antibody production. Third, there can be certain factors in the sera that inhibit antibody production, for example, shed "tumor specific transplantation antigens". Fourth, the determinant can be too small or too similar to the animal's macromolecules to be recognized as foreign.

The antigen binding site of an immunoglobulin is, in many respects, no different from any other macromolecule. Thus, the present invention illustrates that with respect to antigenicity and immunogenicity, portions of the structural configuration of the binding site and of the surrounding region can be antigenic and immunogenic. Such antigenic determinants found in the region of an immunoglobulin binding site are called idiotopes. Often, a binding site region will have several idiotopes.

As explained earlier, "idiotype" is the term used to describe the set of idiotopes expressed in an antibody binding site region. Idiotopes have been shown to be found in the pocket of the binding site and on the surrounding surface. This finding has been confirmed by x-ray diffraction techniques conducted by Giol, *Int. Review of Biochem*, 23, 71 (1979).

Studies of idiotopes have revealed that idiotopes lend themselves to be classified into two natural catagories. In 1968, it was determined that antibodies with similar binding specificities possessed idiotopes unique to themselves as well as idiotopes which they shared with the other antibodies of the same specifity. A study by Schilling et al., *Nature*, 283, 35 (1980) involved 10 hybridoma clones and three myeloma proteins against alpha-1,3-dextran. That study revealed that more than one-half the anti-dextran antibodies shared an idiotope. The study also revealed idiotypes unique to one or a few clones. Idiotypes thus lent themselves to classification into two catagories based on this phenomenon.

The first category of idiotope is the "cross-reactive" or "public" idiotope. The cross-reactive idiotope (CRI) is an idiotope shared by several antibodies of the same specifity. Antibodies to a given antigen generated in different strains of the same species or even different species have been shown to possess the same idiotope.

The second category of idiotope is the "private" or "individual" idiotope. This idiotope is found on only one of a few clones of the antibodies to a given antigen, and is thus, private.

Changes in the amino acid composition of an idiotope do not necessarily change the binding site specificity. Rajewsky et al., *Ann. Rev. Immunol.*, 1, 569 (1983). A single amino acid change in the D gene segment led to loss of one idiotope, modification of a second and loss of six other idiotopes of the parent molecule. However, the antibody still retained its binding site specifity. This finding even applied if the idiotope was located in or near the binding site pocket, also referred to as the complementarity determining region (CDR).

On a final note, an animal typically has over one million antibodies of different binding site specifities. Associated with each binding site specifity is a set of idiotopes. Thus in an animal there is an enormous number of idiotopes.

The present invention employs the technology of raising antibodies against portions of naturally occurring animal proteins using relatively short, chemically synthesized polypeptides. The basic scheme of this technology is as follows.

To begin, the primary sequence of a protein or a portion thereof is determined. This is accomplished in one of several ways. First, the sequence information may have already been determined and is available from the literature. Second, the protein itself can be isolated and directly sequenced, using methods well known in the art. Third, the gene that codes for the protein can be identified using DNA and RNA techniques well known in the art.

The identified gene can then be cloned and isolated using recombinant DNA or RNA technology. The primary amino acid residue sequence of the protein can be determined from the cloned gene in either of two ways. First, the gene itself can be directly sequenced and this information translated into the primary amino acid residue sequence of the protein, all using techniques and information well known in the art. Second, the protein coded from the translated gene can be sequenced.

The next step after determining the primary amino acid residue sequence is to analyze the sequence for regions included in antigenic determinants. This is accomplished using the general knowledge of biochemistry and immunology and specific information on the behavior of the particular protein.

Next, relatively short polypeptide portions of the regions associated with an idiotypic antigenic determinant are chemically synthesized using methods such as those described in Merrified et al., *J. Amer. Chem. Society*, 86, 2149 (1963) or other well-known techniques. The chemically synthesized polypeptide is typically bound to an antigenic carrier as a conjugate and the conjugate is injected in an effective amount as a immunogenic inoculum into a host animal. Small polypeptides, such as those of the present invention, are generally antigenic rather than immunogenic. Standard techniques that are well known by those in the art are used to render the peptide-containing inoculum immunogenic. For example, the peptide containing about 35 residues or more, or a conjugate, can be emulsified in an immunogenic substance, such as an adjuvant. Further, the peptides can be polymerized by known techniques to render them immunogenic.

It is to be understood that when the polypeptides of this invention are utilized to produce antibodies, appropriate methods, as described above, are used to render the peptide immunogenic if it is not immunogenic in the contemplated host as synthesized.

Antisera against the polypeptide can be raised against either the peptide alone, the conjugate or the polymer. While the Fc portion of an antibody of this invention may be useful in some applications, as where it is desirable to preserve the ability of the antibody to bind complement, in most applications only the receptor, idiotype-containing portion, or binding site portion of the antibody is necessary. Therefore, the word "antibody" will be used herein to mean intact antibodies and idiotype-containing portions of antibodies, including the receptor or binding site portion of the antibodies, such as the Fab and F(ab')$_2$ fragments.

The present invention provides a method for producing antisera specific for a defined idiotype of an antibody using synthetic polypeptides. That is, through use of the present invention, synthetic polypeptide technology is employed to produce anti-idiotypic antibodies. The antibodies formed have at least the following characteristics.

First, antibodies are raised to a predetermined specific idiotype. This has not previously been possible.

Second, antisera are raised against idiotypes that are not naturally immunogenic in the animal. That is, the idiotype has the capability of being bound by an antibody (i.e., is antigenic) but does not initiate antibody production against itself (i.e., is not immunogenic).

Third, an anti-idiotypic serum is generated that is useful without need for purification by adsorption.

Additionally, anti-idiotype antibodies of the present invention raised to the second and third CDR of the light chain and third CDR of the heavy chain have further characteristics. First, the antibodies have the capability of distinguishing immunizing polypeptides and determinants on natural proteins (idiotypes) whose corresponding sequences differ by only two amino acid residues. Second, the antisera against these particular CDR have the capability of reacting with both the natural and denatured protein as well as the polypeptide.

One of the uses and benefits of the synthetic peptide and peptide-induced anti-idiotypic antibodies is a means of medicinal immunoregulation and immunodiagnosis.

For example, the urines of patients with rheumatoid arthritis [Gordon et al., *Arthritis Rheum.*, 9, 575 (1966)] and lymphoma [Pierson et al., *Br. J. Cancer*, 41, 681 (1980)] often contain free light chains. The anti-idiotype antibodies of this invention permit a clear-cut assessment of this primary sequence-associated idiotype in the urines of patients with autoimmune and malignant diseases.

Antibodies against urinary light chain idiotypes have been shown to react specifically with neoplastic B lymphocytes. [Tutt et al., *J. Immunol.*, 131, 3058 (1983)] The synthetic peptide-induced anti-idiotypic antibodies against the CRI on human IgM-RF light chains can similarly react with and inactivate RF-bearing B lymphocytes, thereby immunoregulating the patient.

Further, immunization with, for example, a PSL2-protein conjugate can trigger the autologous T cells that regulate autoantibody synthesis. Ample precedent exists for the induction of both suppressor and helper T cells by short peptides [Sakato et al., *Proc. Natl. Acad. Sci. U.S.A.*, 79, 5396 (1982); Jorgensen et al., *J. Exp. Med.*, 158, 2183 (1983)]. Thus, 'synthetic CRI', such as PSL2, can activate the induction of suppressor T cells against RF autoantibodies.

In summary, the snthetic peptide-induced anti-CRI, anti-idiotype antibodies of this invention, provide a new tool for studying the genetic basis of CRI in humans. Since the anti-CRI recognize only primary sequence-dependent determinants, they in essence identify phenotypic markers of the corresponding variable region genes. The peptide-induced anti-CRI thereby render unnecessary the breeding experiments that originally defined the genetic basis of CRI in animals. It has been shown that a RF-CRI is inherited among related members of a family. [Pasquali et al., *J. Clin. Invest.*, 66, 863 (1980)]. The synthetic peptide-induced anti-CRI can thus help to delineate the genetic basis for the familial clustering of autoantibody-CRIs in patients with abnormal autoantibody production.

In particular, the eight synthetic peptides listed in Table 14, corresponding to heavy chain CDR sequences on human IgM-RF paraproteins, have been assessed to evaluate their ability to elicit specific anti-idiotypic antibodies. As discussed in detail in Section V, at least two different rabbit antisera were generated against each of eight different synthetic peptide-KLH conjugates, representing all three heavy chain CDRs of two monoclonal IgM-RFs (Sie, Pom), and the second and third CDRs of an additional IgM-RF (Wol). In all cases, potent and specific anti-peptide antibodies were produced. However, only the antisera against the third heavy chain CDRs reacted consistently with the corresponding heavy chain polypeptides, and with the intact IgM-RF proteins. These results with synthetic peptides strongly suggest that the third heavy chain CDR sequence is associated with an immunodominant idiotypic determinant.

In the well-defined murine anti-dextran [Clevinger et al., *J. Exp. Med.*, 151, 1059 (1980)], anti-phosphocholine [Berek, *Eur. J. Immunol*, 14, 1043 (1984)], anti-galactan [Rudikoff et al., *J. Exp. Med.*, 158, 1385 (1983)], and anti-arsonate [Gridley et al., *J. Immunol*, 134, 2, 1236 (1985)] antibody systems, the heavy chain D region segment has been shown to play an important role in the generation of immunodominant idiotypes. The D region is responsible for the majority of the sequence variability in the third CDR of mouse heavy chains, but often contributes little to antigen binding specificity. (Clevinger et al., supra.; Rudikoff et al., supra.).

In this regard, it is interesting to note that the third heavy chain CDR may present an exposed, accessible surface on the immunoglobulin molecule, as predicted by computer modeling. (Rudikoff et al., id.). In human heavy chains, the D region boundaries are less well defined. [Siebenlist et al., *Nature*, 294, 631 (1981); Kabat et al., U.S. Dept. of Health and Human Services (1983)]. However, it seems likely that the human D segment does constitute part of the third heavy chain CDR, and contributes to its variability. A major function of antibody D region gene segments may be to generate idiotypic diversity, independently of effects on antigen binding.

The ability of synthetic peptides to delineate the role of the heavy chain D segment, and the third CDR, in the formation of immunodominant idiotypes has clinical implications. Specifically, peptide-induced anti-idiotypes provide a means for comparing the primary structures of immunoglobulins of unknown sequence. However, to be useful for the specific modulation of abnormal immunoglobulin production, the peptide-induced antibodies must recognize the intact cognate protein in its native form. Results discussed in detail hereinafter suggest that synthetic peptides corresponding to the third CDR of human heavy chains and the second and third CDRs of human light chains can reproducibly elicit anti-idiotypic antibodies against intact human IgM-RF paraproteins.

Further, an anti-idiotype to human monoclonal IgM anti-IgG autoantibodies (rheumatoid factors) was found to react also with human IgG. [Bona et al., *J. Exp. Med.*, 156, 986 (1982)]. This peculiar anti-idiotype was called an 'epibody' and was induced by immunization with IgM-RF Glo. The induction of a similar epibody was achieved by immunization with a synthetic peptide designated PGL1 (corresponding to the first CDR of the light chain of the IgM-RF Glo). Those results confirm the existence of epibodies, and provide the possible molecular basis of the epibody phenomenon.

It will be understood that while there are many procedural steps utilizing many materials in the manufacture of the inocula, of which vaccines are one type, and anti-idiotypic antibody preparations of this invention, as discussed in detail hereinafter, the invention is not limited to the utilization of any particular steps or reagents or conditions.

II. Discussion

As discussed generally before, the antigen binding site of an antibody is formed from the three-dimensional folding of the variable regions of the heavy and light chains. Padlan et al., *Nature, New Biol*, 245, 165 (1973). Diversity in antibody specificity is derived from variation in the primary (linear) amino acid residue sequences of the variable regions. The primary amino acid residue sequence dictates the three-dimensional folding pattern. Thus, different "shape" binding sites with different active residues in the binding site are generated from different primary amino acid residue sequences. There are three regions of extreme variability in the primary sequence within the variable region. These sites are termed hypervariable regions and contain the complementarity-determining region (CDR) whose amino acid residues converge at the level of tertiary structure to form the combining site. [Capra et al., *Proc. Nat. Acad. Sci. U.S.A.*, 71, 845 (1974)].

As described herein, the anti-idiotypic antibodies of the present invention were raised against polypeptides that substantially immunologically correspond to primary amino acid residue sequences in the heavy and light chain variable regions of particular IgM-RF immunoglobulins. The present invention can be applied to manipulating the immune response to diagnose, cure or combat diseases of the immune system.

Specifically, the synthetic peptide-induced anti-idiotype antibodies against idiotypic antigenic determinants including at least a portion of a complementarity determining region of a human IgM-RF immunoglobulin can be administered to or induced in a human with an autoimmune disease. These antibodies can react with and inactivate RF-bearing B lymphocytes. Further, immunization with synthetic peptides of this invention can induce production of autologous T cells that regulate autoantibody synthesis.

As stated before, antibodies against urinary light chain idiotypes react with neoplastic B cell lymphocytes. Antibodies of this invention react with heavy or light chain idiotypes of various antibodies, in particular, human rheumatoid factors, as described in detail below. These antibodies can similarly react with RF-bearing B lymphocytes.

Further, as explained in detail below, synthetic polypeptides of this invention induce the production of anti-idiotype antibodies specific for the CDR to which the peptide amino acid residue sequence corresponds. Similarly, peptides of this invention can induce production of autologous T cells that regulate autoantibody synthesis.

In a like manner, this invention can be used to reduce transplant rejections. Such application of the invention is further explained below.

Invasion by an antigenic substance generally results in a polyclonal response to the antigen as described by Hansburg et al., *J. Immunol.*, 194, 1406 (1977); Briles et al., *J. Exp. Med.*, 152, 151 (1980) and Ceney et al., *J. Immunol.*, 128, 1885 (1982).

A polyclonal response is likely to occur for two reasons. First, an antibody or the receptor on a B-cell has a precise specificity. However, antibodies and B-cell receptors have the capability of reacting to antigenic determinants that do not exactly match the binding site "shape" but are related in "shape". This is known as cross-reactivity.

Thus, a particular antigen is likely to fall within the range of cross-reactivity of several B-cell clones. Consequently, several antibodies with different variable regions are produced against an antigenic determinant.

Second, an antigen (immunogen) is likely to possess several antigenic determinants. Each of these antigenic determinants is likely to elicit its own antibody response, thereby producing antibodies that contain different variable regions.

In summary, invasion by an antigenic foreign substance results in a polyclonal antibody response. These antibodies do not all share identical variable regions. This in turn results in a variety of idiotypes being expressed by the antibodies directed against an antigen.

As described herein, synthetic polypeptides, corresponding to hypervariable regions of the heavy and light chains of human monoclonal IgM-RFs (paraproteins), have been used to induce the production of anti-hypervariable region (anti-idiotype) antibodies.

For example, the anti-idiotypic antibody induced by synthetic peptide PSL2 (which corresponds to the second CDR of RF Sie binds to the intact immunoglobulin molecule (Sie) and to its isolated chains, but does not bind to other IgM paraproteins or to pooled human IgG. Moreover, the binding of the antibody to the intact IgM was inhibited specifically by the free polypeptide.

These results also demonstrate that a specific anti-idiotypic antibody of predefined specificity; i.e., that binds to a particular idiotypic antigenic determinant, can be induced by a synthetic polypeptide, and that such an anti-idiotypic antibody recognizes an idiotypic antigenic determinant formed by the known hypervariable region on the intact immunoglobulin. In one embodiment of the present invention, that predefined specificity does not extend beyond recognition of a private idiotype of a single antibody molecule.

In a preferred embodiment, however, the use of synthetic polypeptides to induce the production of anti-idiotypic antibodies has been extended to generate an anti-idiotypic antibody of a public or cross-reactive idiotype. Among human monoclonal IgM rheumatoid factors (IgM-RF), two major cross-reactive idiotypes (e.g., Wa and Po) have been described. [Kunkel et al., J. Exp. Med., 137, 331 (1973)]. The Wa group includes 60% of monoclonal IgM-RFs, and the expression of the Wa cross-reactive idiotype was thought to depend on the L chains of reactive IgM-RF. [Kunkel et al., J. Exp. Med., 139, 128 (1974) and Andrews et al., Proc. Natl. Acad. Sci., U.S.A., 78, 3799 (1981)].

A murine monoclonal antibody (designated mab 17-109) has been prepared that reacts with two cross-reactive (+) idiotypic IgM-RFs (e.g., Sie and Glo), but not with two Wa-cross-reactive (−) idiotypic IgM-RFs (e.g., Lay and Pom). [Carson et al., Mol. Immunol., 20, 1081 1983)]. In addition, mab 17-109 reacted with the light chains, but not with the heavy chains, of Wa-cross-reactive (+) idiotypic IgM-RFs. A comparison of the reported amino acid residue sequences of the L chains of Wa-cross-reactive (+) idiotypic IgM-RFs (See FIG. 3) indicates that these L chains have the same amino acid residue sequence in the second hypervariable region. Thus, a synthetic polypeptide corresponding in sequence to the amino acid residue sequence of that region, designated PSL2, was prepared and was used to induce the production of an anti-idiotypic antibody of a cross-reactive hypervariable region.

Further, synthetic peptides described in Table 1 (hereinafter) have been used to generate eight specific anti-idiotypic antibodies [in addition to one anti-PGL1 as described in Chen et al., J. Exp. Med., 161, 323 (1985) and discussed in Section V, herein]. Using these reagents, the majority of human monoclonal IgM-RFs were demonstrated to share two CRI on the light chains, suggesting strongly that the genetic basis of these RF light chains is very restricted. In fact, amino acid residue sequence analysis revealed that four RFs bearing both PSL2- and PSL3-CRIs have identical sequences in the whole i $V_k$ gene region. [Pons-Estel et al., J. Exp. Med., 160, 893 (1984)]. In addition, five more RFs bearing the PSL2-CRI have almost identical sequences, with one to four different amino acid residues per RF light chain. [Andrews et al., Proc. Natl. Acad. Sci. U.S.A., 78, 3799 (1981)].

In contrast to the homologous RF light chains, the RF heavy chain-associated idiotypes are extremely private. Four anti-idiotypes (induced by PWH2, PWH3, PPH2, and PPH3) react only with the corresponding parent proteins, while the fifth one (induced by PSH3) reacts weakly with an additional nonparent protein (an IgM-RF designated Gal). These results suggest either that RF heavy chains are encoded by a larger number of $V_H$ and $D_H$ genes, or that RF heavy chains have an unusually high frequency of somatic mutation in the H2 regions of a limited number of $V_H$ genes and significant variation in the V/D/J junction.

Detailed analysis of idiotypes has revealed that CRI represent phenotypic markers of the respective germ-line V genes. [Rajewsky et al., Ann. Rev. Immunol. 1, 569 (1983); Capra et al., Immunol. Today, 4, 177 (1983)]. For light chains, the $V_L$ genes encode amino acid residues up to about position 95 (i.e. including 2/3 of CDR3 region). [Sakano et al., Nature, 280, 288 (1979); Max et al., Proc. Natl. Acad. Sci. U.S.A., 76, 3450 (1979)]. In contrast, $V_H$ genes encode amino acid residues up to about position 94, the last amino acid residues of the third framework region; and the genes of the third CDR of heavy chains (H3) are composed of $D_H$, $J_H$ and nucleotides of unknown origins. [Early et al., Cell, 19, 981 (1980); Sakano et al., Nature, 286, 676 (1980); Sakano et al., Nature, 290, 562 (1981)].

Although only five to ten $D_H$ genes and five $J_H$ genes have been identified in humans and mice, the 'imprecise' joining at the V/D and D/J junctions plus nucleotides of unknown origins together make the H3 the most heterogenous regions among the six CDR of both heavy and light chains. [Sakano et al., Nature, 290, 562 (1981); Sienbenlist et al., Nature, 294, 631 (1981); Kurosawa et al., J. Exp. Med., 155, 201 (1982)]. This is best demonstrated by the sequence analysis of eight IgM anti-galactan antibodies [Rudikoff et al., J. Exp. Med. 158, 1385 (1983); Pawlita et al., J. Immunol., 129, 615 (1982)]. Thus, it is not surprising to see that all three H3-associated idiotypes (CDRs 1, 2, and 3) of RF molecules are private.

Compared with the very heterogeneous H3 region, the H2 region sequences were identical in seven out of eight IgM anti-galactan antibodies. [Rudikoff et al., J. Exp. Med., 158, 1385 (1983)]. It should be noted that, among these eight antibodies: 1) all are encoded by a single $V_H$ gene [Tonegawa, Nature, 302, 575 (1983)], in particular, four have identical amino acid sequences through the whole $V_H$ region; 2) seven of them have identical sequences through the whole $V_K$ region [Pawlita et al., J. Immunol., 129, 615 (1982)]. In light of this report, that both H2-associated idiotypes studied (CDRs 2 and 3) are unique among 14–15 RFs strongly suggests that the RF may employ a relatively large number of $V_H$ genes.

In summary, using the eight synthetic CDR peptide-induced anti-idiotypes, 70% of monoclonal human IGM-RFs were shown to share two light chain-associated CRI (corresponding to PSL2 and PSL3), while all five heavy chain-associated idiotypes (corresponding to PSH3, PWH2, PWH3, PPH2 and PPH3) are private among 14-17 IgM-RF analyzed. (Anti-PSH2 antibodies reacted only with the peptide.) These results reveal that the majority of IgM-RF share homologous light chain variable regions, but have heterogenous heavy chain variable regions. In addition, they suggest that the IgG-binding activities of RF depend mainly on the specific light chain sequence, and that a large number of $V_H$ genes are used in generating RF autoantibodies.

To further characterize the CDRs of human IgM-RF, two additional synthetic polypeptides of this invention, synthetic CRI corresponding to CRI 1 of the heavy chains of IgM-RF Sie and IgM-RF Pom, were used to induce anti-idiotype antibodies. As will be discussed in detail hereinafter, antisera raised against synthetic peptides corresponding to the third heavy chain CDR consistently recognize idiotypes expressed by intact IgM-RF autoantibodies. In contrast, high titer antibodies against synthetic peptides representing the first and second heavy chain CDR infrequently bind to the IgM-RF molecule. These results suggest a distinctive role of the D region in the generation of idiotypic determinants, and have implications concerning the manipulation of idiotype-anti-idiotype reactions in patients.

Further, an anti-idiotype with "epibody" properties against the human monoclonal IgM-RF Glo was generated by immunization of a rabbit with a synthetic peptide (PGL1), corresponding to the first CDR of the Glo kappa light chain. The antibody reacted specifically with both the PGL1 and the intact IgM-RF Glo.

When analyzed by the immunoblot method, the anti-PGL1 antibody recognized the isolated kappa chains of the IgM-RF paraproteins Glo, Gar, Got, and Pal, but not the kappa chains of IgM-RF Lay. The anti-PGL1 antibody did not bind detectably to the heavy chains of any IgM-RF. The binding of the antiserum to the Glo kappa chain was completely inhibited by the free PGL1 peptide, but not by a control peptide (PSH3).

Thus, the synthetic PGL1 peptide induced an anti-idiotype antibody against a cross-reactive idiotype associated with the kappa chains of several human IgM-RF autoantibodies. The molecular basis of this cross-reactive idiotype is defined by the PGL1 amino acid sequence.

Initial observations of the anti-PGL1 antibody were surprizing and disappointing in that the induced antibody bound with the gamma chain of the pooled human IgG. However, the epibody described by Bona et al., *J. Exp. Med.*, 156, 986 (1982), prompted further study of the exact specificities of this peculiar antiserum.

The epibody was defined by Bona et al., supra., as an anti-idiotype antibody that reacted with the antigen of the idiotype-bearing antibody. Studies were done to demonstrate that a portion of the PGL1-induced 'polyclonal' anti-idiotype did react additionally with human IgG, as a regular antibody reacts with its antigen.

FIG. 18 shows that the binding of PGL1-induced anti-idiotype with IgG gamma chain was partially inhibited by PGL1 peptide; suggesting that there are at least two sets of anti-gamma components in the induced polyclonal antiserum, and that only one set recognizes the PGL1-associated epitope on the IgG gamma chain. FIG. 20 shows that both sets of anti-gamma antibodies in the serum can be adsorbed by, and eluted from, a human IgG column, demonstrating that they react with intact IgG molecules.

In addition, the anti-PGL1 antibodies, previously adsorbed with a human IgG column, still reacted with the Glo light chains. In contrast, the human IgG column eluate of anti-PGL1 antisera that was subsequently passed through a PGL1 column reacted only with IgG, and not Glo. By pooling these data, the anti-PGL1 antibodies can be classified as follows (Table 17, hereinafter): (a) conventional anti-idiotype that reacts with Glo light chain only, and whose antibody reactivity is completely inhibited by PGL1; (b) epibody that reacts with both Glo light chain and IgG, and whose antibody reactivity is inhibitable by PGL1; and (c) anti-IgG antibody that reacts with IgG only, and whose binding is not inhibitable by PGL1.

It should be pointed out that the epibody constitutes only a very small portion of the overall anti-PGL1 antibodies, that its binding to the separated Glo light chain and IgG gamma chain is of low affinity, and that the binding to intact Glo and intact IgG is of even lower affinity. The anti-IgG component was induced indirectly, possibly through the immune network or other unknown mechanisms.

Other than the original description by Bona et al., supra., the existence of epibodies has not been confirmed, so their biological significance could not be investigated. The PGL1-induced antibodies confirm independently the existence of epibodies. Moreover, it is likely that the structural basis of the epibody described here is the Ser-Ser-Ser sequence shared by the reactive IgM-RF (Glo and Gar) and human IgG molecules [residues 195-197, numbering according to Kabat et al., Sequences of Proteins of Immunological Interest, Dept. of Health and Human Services (1983)]. This is based on the following: (a) anti-PGL1 recognizes mainly a determinant consisting of Val-Ser-Ser-Ser (FIG. 19); (b) anti-idiotypes, induced by a similar peptide PSL1 (which corresponds to the first CDR of Sie light chain and is identical to PGL1 except for having Asn instead of Ser at position 9), did not react with human IgG; (c) anti-PGL1 reacted with the F(ab')2, but not Fc, of the human IgG; and (d) three of six gamma chains with known sequences (Eu, Nie, and IgG G4) have Ser-Ser-Ser at position 195-197, while neither one of two mu chains (Gal and Ou) have Ser-Ser-Ser sequence.

Numerous investigations using dextran and homopolymers of amino acids have concluded that the antibody-combining site can accommodate a hexasaccharide or tetrapeptide. [Goodman, In Basic and Clinical Immunology, Stites et al. (1982), Lange Medical Publications, Los Altos, Calif.]. In addition, analysis of the antigenic determinant size of the protein antigens revealed that a determinant consisted of a pentapeptide or a tetrapeptide. [reviewed in Benjamini et al., Curr. Top Microbiol. Immunol, 58, 85 (1972)].

Moreover, in the case of C-terminal pentapeptide of tobacco mosaic (TMV) virus, Leu-Asp-Ala-Thr-Arg, the Leu-Asp could be replaced by N-octanoyl. [Benjamini et al., Biochemistry, 1, 1261 (1968)]. This work suggested that the anti-TMV antibodies recognized specifically the tripeptide Ala-Thr-Arg, while the Leu-Asp enhanced the antibody binding by providing hydrophobicity.

Thus, the loss of idiotype in the IgM-RF Pay can be explained by the decreased hydrophobicity, due to the Val to Lys substitution at position 28. Similarly, it is interesting to note that IgG has Val-Pro at the N-terminal to Ser-Ser-Ser. [Kabat et al., Sequences of Proteins of Immological Interest, Dept. of Health and Human Services (1983)].

III. Diagnostics

The synthetic polypeptides and antibodies induced by (raised to) them can also be used as a portion of a diagnostic composition for detecting the presence of antigenic proteins and antibodies.

A diagnostic reagent system embodying this invention is useful for the determination of the presence of RF. Further, the diagnostic reagent system can be used to characterize RF to study various autoimmune disease states.

A diagnostic system for assaying for the presence of an antigenic determinant of an immunoglobulin includes at least one container that contains an effective amount of an antibody of this invention. That is, the antibody used in the system is induced by a synthetic polypeptide having an amino acid residue sequence that immunologically corresponds substantially to a primary amino acid residue sequence of an antigenic determinant of the immunoglobulin to be assayed.

The diagnostic system provides an antibody induced by a peptide of the invention. A predetermined amount of the antibody is admixed with a predetermined amount of a sample to be assayed for the presence of the idiotypic antigenic determinant to form an admixture. The admixture is maintained for a period of time sufficient for the antibody to immunoreact with and bind to an idiotypic antigenic determinant that may be present in the admixture. The amount of binding between the antibody and the determinant is determined.

In a preferred method the antibody induced by a peptide of this invention is affixed to a solid support. Exemplary preferred solid supports include microtiter dishes and latex particles. The solid support-affixed antibody and an aliquot of a sample to be assayed for an idiotypic antigenic determinant of an immunoglobulin are admixed to form a liquid-solid phase admixture. The admixture is maintained for a period of time sufficient for the antibody to react with determinant that may be present in the admixture. The amount of immunoreaction between the antibody and the determinant are determined.

This determination can be performed by several known techniques. For example, the rate of agglutination is measured when the antibody is affixed to a latex particle. Alternatively, when the antigenic determinant is on an intact immunoglobulin, second antibodies specific for the class and species of immunoglobulin can be linked to indicators such as enzymes, radioisotopes and fluorochromes. Also, indicator-affixed synthetic peptide can be added and the amount of immunoreaction can be determined from competitive inhibition as described hereinafter. It is preferred that when using second antibodies or competitive inhibition the liquid and solid phases of the admixture be separated before determining the amount of immunoreaction.

In another embodiment, the system comprises in separate containers (a) a first reagent and (b) a second reagent both in biologically active form, along with an indicating group.

The first reagent contains one of the before-described synthetic polypeptides, a combination of such polypeptides, or conjugates prepared therefrom. The second reagent includes polyamide-containing idiotypic regions of antibodies raised to the synthetic polypeptides or their conjugates. The idiotype-containing polyamides of the second reagent can be substantially intact antibodies induced by peptides of this invention or can be processed to provide Fab or F(ab')$_2$ antibody fractions whose preparations are described before, e.g., by pepsin digestion. [Nisonoff et al., Methods Med. Res., 20, 134 (1964)]. An indicating group can also be provided in the system and can be initially bound to or free from either of the two reagents.

Admixture of predetermined amounts of the first and second reagents in the presence of a predetermined amount of a body component to be assayed results in an immunoreaction. The degree or amount of the immunoreaction so produced is different from a known immunoreaction amount when either of the reagents, typically an idiotype-containing polyamide (such as a naturally occurring RF), is present in the body component. The amount of immunoreaction is typically diminished due to competitive inhibition of the reagent idiotype-containing polyamide by idiotype-containing polyamide present in the body component.

Another diagnostic system comprises the before-discussed anti-idiotype antibodies in biochemically active form and an indicating means. In this system, the anti-idiotype antibodies or their Fab or F(ab')$_2$ fractions react with an antigen containing the idiotypic antigenic determinant for which the anti-idiotype antibody is specific in a sample to be assayed to form an immunoreactant whose presence is signalled by the indicating means.

The above system can also include second antibodies raised to antibodies of the same class and from the same species as the anti-idiotype antibodies as part of the indicating means. For example, where the anti-idiotype antibodies are raised in rabbits, commercially available goat anti-rabbit antibodies can be used. Such second antibodies conveniently include a label such as a linked enzyme, for example, horseradish peroxidase or alkaline phosphatase; a radioactive element, for example, $^{125}$I; or a fluorochrome, such as fluoroscein isothiocyanate, as the signal indicator.

Exemplar diagnostic reagent systems include enzyme-linked immunosorbent assays (ELISA) wherein the system assays the determinant directly or by competitive inhibition with, for example, the synthetic peptide, and radioimmunoassays based on either direct assay or competitive inhibition.

IV. Inocula

The present invention further contemplates the use of synthetic peptides of this invention as immunoregulatory agents to treat autoimmune and other diseases of the immune system. Autoimmune diseases include, for example, autoimmune hemolytic anemia; endocrine diseases such as Hashimotos thyroiditis and Graves disease; rheumatic diseases, such as rheumatic fever, rheumatoid arthritis, systemic lupus (erythematosus, and Sjogren's syndrome; and myasthenia gravis. Other diseases of the immune system include, for example, malignancies of the immune system organs, allergies, transplant rejections and the like.

As discussed previously, synthetic polypeptides can be used to generate anti-idiotype antibodies that are specific for cross-reactive or private idiotypes on IgM-RF immunoglobulins. These anti-idiotypes bind to idiotype-containing RF on lymphocytes and can inactivate the RF-bearing lymphocytes. The polypeptides can be used to produce anti-idiotype antisera in an animal having an autoimmune disease or used to produce anti-idiotype antisera in another, preferably homologous, animal, and can be passively administered to an animal having an autoimmune disease.

The inoculum additionally triggers the production of autologous T cells that regulate autoantibody synthesis. The inoculum thus produces two responses by the host animal immune system that immunomodulate the autoimmune disease.

The inocula are further useful to produce antibodies for use in diagnostics of this invention by similar methods.

The inocula used herein contain an effective amount of either a polypeptide immunogen alone, or as a polymer of individual polypeptides such as when linked together through reaction with glutaraldehyde, or a polypeptide linked to an antigenic carrier. Polymeric polypeptides can also be prepared by addition of cysteine residues at both polypeptide termini followed by oxidation as with atmospheric oxygen at moderate pH values such as between about pH 7 and pH 10. The stated amounts of polypeptides refer to the weight of polypeptide without the weight of a carrier, when a carrier is used.

As explained before, when the polypeptide alone is not immunogenic it must be conjugated to a carrier, polymerized or the like to render it immunogenic.

An inoculum also contains a physiologically tolerable vehicle such as distilled or deionized water, saline, a buffered salt solution such as phosphate-buffered saline or Ringer's lactate or a physiologic sugar solution such as 5% dextrose in water in which the immunogenic polypeptide is dispersed. Inocula further typically include an adjuvant. Complete Freund's adjuvant (CFA), incomplete Freund's adjuvant (IFA), and alum are adjuvants well known in the art, and are available commercially from several sources.

Inocula dispersions were prepared with IFA or CFA as follows. An amount of the synthetic polypeptide, polymeric polypeptide or conjugate sufficient to provide the desired amount of polypeptide per inoculation was dissolved in isotonic phosphate-buffered saline (PBS). Equal volumes of CFA or IFA were then mixed with the polypeptide solution to provide a vaccine (inoculum) containing polypeptide, water and adjuvant in which the water-to-oil ratio was 1:1. The mixture was thereafter homogenized to provide the vaccine (inoculum) stock solution.

The term "inoculum" and its various grammatical forms is used herein as a general phrase for an immunogen-containing aqueous composition designed to induce the production of antibodies. The term "vaccine" and its various grammatical forms is used herein to describe an inoculum in which the antibodies induced are used within the host animal in which they are induced, or in an animal of the same species. It is to be understood that any inoculum contains an amount of immunogen effective to induce production of antibodies. Immunogen-containing inocula can also be prepared with keyhole limpet hemocyanin (KLH), KLH in IFA (incomplete Freund's adjuvant), alum, KLH-alum absorbed, KLH-alum absorbed-pertussis, edestin, thyroglobulin, tetanus toxoid and tetanus toxoid in IFA, and the like.

Upon injection or other introduction of the antigen or immunogen into the host, the host's system responds by producing large amounts of antibody to the antigen. Since the specific idiotypic antigenic determinant of the manufactured antigen; i.e., the antigen formed from the synthetic polypeptide and the carrier and the like, is the same as or is an immunological surrogate for the determinant of the natural antigen of interest, the host becomes immune to a natural antigen having a immunologically sufficiently similar shape to the shape of a polypeptide. The shapes are sufficiently similar when the inducing peptide has the same amino acid sequence as the primary sequence of the second and third CDR of the light chain or the third CDR of the heavy chain of an IgM-RF.

The effective amount of polypeptide per inoculation depends, inter alia, on the animals inoculated, body weight of such animals and the chosen inoculation regimen. Immunogen-containing inocula are typically prepared from the dried solid polypeptide by suspending the polypeptide in water, saline, buffer or adjuvant, or by binding the polypeptide to a carrier and suspending the carrier-bound polypeptide (conjugate) in a similar physiologically tolerable vehicle such as an adjuvant. An effective amount of polypeptide present in an inoculum such as a vaccine can be from about 20 micrograms to about 500 milligrams per inoculation, exclusive of any carrier used.

It is frequently convenient to add one or more additional amino acids to the amino- or carboxy-termini of the synthetic polypeptide to assist in binding the synthetic polypeptide to a carrier to form a conjugate. Cysteine residues added at the carboxy-terminus of the synthetic polypeptide have been found to be particularly useful for forming conjugates via disulfide bonds and Michael-type addition reaction products, but other methods well known in the art for preparing conjugates may be used. Exemplary binding procedures include the use of dialdehydes such as glutaraldehyde and the like, or the use of carbodiimide technology as in the use of a water-soluble carbodiimide, e.g. 1-ethyl-3-(3-dimethylaminopropyl) carbodiimide.

Useful antigenic carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, as well as polyamino acids such as poly(D-lysine:D-glutamic acid), and the like.

As is also well known in the art, it is often beneficial to bind the synthetic polypeptide to its carrier by means of an intermediate, linking group. As noted above, glutaraldehyde is one such linking group, while when cysteine is utilized, the intermediate linking group is preferably a m-maleimidobenzoyl N-hydroxysuccinimide ester (MBS). MBS is typically first added to the carrier by an ester-amide interchange reaction. Thereafter, the above Michael-type reaction can be followed, or the addition can be followed by addition of a blocked mercapto group such as thioacetic acid ($CH_3COSH$) across the maleimido-double bond. Cleavage of the blocking (acetyl) group follows, and then a disulfide bond is formed between the deblocked linking group mercaptan and the mercaptan of the added cysteine residue of the synthetic polypeptide.

The choice of carrier is more dependent upon the ultimate intended use of the antigen than upon the determinant of the antigen, and is based upon criteria not particularly involved in the present invention. For example, if an inoculum is to be used in non-human animals, a carrier which does not generate an untoward reaction in the particular animal will be selected. If an inoculum is to be used in man, then the overriding matters relate to lack of immunochemical or other side reaction of the carrier and/or the resulting antigen, safety and efficacy—the same considerations that apply to any vaccine intended for human use.

It is very often desirable to determine if a particular antigen is present as an aid, for example, in the diagnosis of a particular disease. Because the synthetic antigen is mono-specific to the single specific antigenic determinant of interest, antibodies to the antigen are also mono-specific to the antigen of interest. Perfect mono-specificity may not always be accomplished, but cross-referencing to other antigenic portions of the antigen is avoided because only one immune response is possible by the antibody.

V. RESULTS

Synthetic peptides having amino acid residue sequences corresponding to primary amino acid residue sequences of idiotypic antigenic determinants including at least a portion of the complementarity-determining regions (CDR) of immunoglobulin molecules have been used to induce anti-idiotypic antisera. In particular, polypeptide PSH3 (corresponding to the third CDR of a human RF paraprotein, designated Sie, heavy chain) induced an anti-idiotypic antibody which reacted with only one out of five IgM rheumatoid factors (RFs) (see FIGS. 2,4,5,6,10 and 11), while polypeptide PSL2 (corresponding to the second CDR of Sie light chain) induced an anti-idiotypic antibody that identified a cross-reactive idiotype (CRI) expressed by ten out of twelve human IgM-RFs analyzed (See FIGS. 4,5,6 and 7).

Five additional anti-idiotypic antibodies were generated by immunization with the peptides PSL3 (Sie light chain third CDR), PWH2 and PWH3 (WOL heavy chain second and third CDR, respectively), PPH2 and PPH3 (Pom heavy chain second and third CDR, respectively). As analyzed by immunoblot assay, both anti-PSL3 (see FIGS. 7, 8 and 9 ) and anti-PSL2 (see FIGS. 4C and E and 7) reacted with the majority of sixteen IgM-RFs. In contrast, all five anti-idiotype antibodies induced by polypeptides corresponding to sequences of the second and third CDRs of the heavy chain peptides reacted only with the parent proteins, except anti-PSH3 which reacted weakly with one additional RF (see FIGS. 10 through 14). These results indicate that the majority of human monoclonal IgM-RFs probably employ only a single $V_L$ (RF) gene for light chains, but a large number of $V_H$ genes for heavy chains.

The specific peptides studied are listed in Table 1. Table 2 lists amino acids and their three and one letter symbols used in the art to represent each amino acid.

TABLE 1
THE AMINO ACID SEQUENCES OF THE SYNTHETIC PEPTIDES

| Peptide Name | Protein | Residue No[b] | Amino Acid Sequence[c] |
|---|---|---|---|
| 1. PSL2 | Sie | 49–61 | YGASSRA<u>TGIPDR</u> (C) |
| 2. PSL3 | Sie | 88–99 | C<u>QQYGSSPQTFG</u> |
| 3. PSH2 | Sie | 49–65 | <u>G</u>SPAKWTDPFQGVYIKWE (GGC) |
| 4. PSH3 | Sie | 95–102 | EWKGQVNVNPFDY (GGC) |
| 5. PWH2 | Wol | 49–65 | GQIPLRFNGEVKNPGSVV (GGC) |
| 6. PWH3 | Wol | 95–102 | EYGFDTSDYYYY (GGC) |
| 7. PPH2 | Pom | 49–65 | AWKYENGNDKHYADSVNG (GGC) |
| 8. PPH3 | Pom | 95–102 | DAGPYVSPTFFAH (GGC) |

[a]The first letter 'P' designates that the code named material is a synthetic peptide; the second letter designates the corresponding parent protein; the third letter designates the heavy (H) or light (L) chains; the numeral designates the CDR, the idiotypic antigenic determinant of the IgM-RF.
[b]Position number from the amino-terminus according to Kabat, U.S. Dept. of Health and Human Services; (1983).
[c]The amino acid sequences as reported by Capra and his colleagues [(Proc. Natl. Acad. Sci. USA, 71 4032 (1974); and Proc. Natl. Acad. Sci. USA, 78, 3699 (1981)]. The underlined residues belong to the adjacent framework regions (FR), and the residues within the parentheses were added to the C-terminus for coupling purposes.

TABLE 2
TABLE OF CORRESPONDENCE

The full names for individual amino acid residues are sometimes used herein as are the well-known three-letter abbreviations. The one-letter symbols for amino acid residues are used herein most often. The Table of Correspondence, Table 2 below, provides the full name as well as the abbreviation and symbols for each amino acid residue named herein.

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Induction of Anti-peptide PSH3 Antibodies

After receiving two subcutaneous injections of synthetic polypeptide PSH3-KLH conjugates of this invention in CFA, and one injection of glutaraldehyde cross-linked polypeptide PSH3 in IFA over a time period of about two to three months, to induce antibody production, as described later. The rabbits were bled and the sera were analyzed for anti-polypeptide activity by the ELISA method. Sera from two immunized rabbits contained anti-polypeptide antibody detectable at dilutions as high as 1:100,000 as is shown in Table 3. Control sera from normal rabbits did not bind significantly to the synthetic polypeptide PSH3-coated plates.

TABLE 3
INDUCTION OF ANTI-IDIOTYPE ANTIBODIES BY A SYNTHETIC POLYPEPTIDE PSH3 THAT SUBSTANTIALLY CORRESPONDS IMMUNOLOGICALLY TO AN IDIOTYPIC ANTIGENIC DETERMINANT OF HUMAN IgM RHEUMATOID FACTOR (Sie)[a]

| Serum Dilution | Absorbance Values at 405 nanometers ($\times 10^3$) | | | |
|---|---|---|---|---|
| | $10^{-3}$ | $10^{-4}$ | $10^{-5}$ | Control |
| Normal Rabbit | 25 | 0 | 0 | 4 |
| Immune Rabbit 1 | 1023 | 497 | 95 | 5 |
| Immune Rabbit 2 | 937 | 530 | 85 | 0 |

[a]The activities of synthetic polypeptide PSH3-induced anti-idiotypic antibodies (as described above) of two immune rabbit sera were assayed as described herein by a solid phase ELISA on a polypeptide PSH3-coated polyvinyl chloride microtiter plate. Duplicate microtiter wells were coated with the peptide [100 micrograms per milliliter of borate-buffered saline (BBS)] to form the solid phase, and various dilutions of the rabbit antisera were added to form solid/liquid phase admixtures. Control wells contained buffer only. After incubation (maintenance of the solid/liquid phase admixtures so formed) for a time period of three hours to permit immunoreaction between the solid phase-bound antigen and serum antibodies in the liquid phase, and then washing, the amount of bound antibody was determined with alkaline phosphatase-conjugated goat anti-rabbit IgG. An aqueous compostion of the enzyme-conjugated antibody was admixed with the wells to form a further solid/liquid phase admixture. That admixture was maintained for a time sufficient for the admixed antibodies to immunoreact with bound rabbit antibodies. The solid and liquid phases were separated again and an aqueous substrate solution was added. The absorbance value at 405 nanometers of the reacted enzyme substrate was measured after one hour.

Reactivity of Anti-polypeptide PSH3 Antibody with the Intact Antibody Molecule IgM-RF (Sie)

The anti-polypeptide PSH3 antisera were assayed for direct binding to plates coated with intact IgM-RF (Sie). Table 4 shows that both anti-polypeptide antisera, but not control sera, reacted with the intact antibody molecule. Even at 1.100,000 dilution, the anti-polypeptide sera bound significantly to the intact IgM protein having an idiotypic antigenic determinant including an amino acid residue sequence substantially immunologically corresponding to the synthetic polypeptide used to induce the anti-polypeptide antibodies In the sera.

TABLE 4
REACTIVITY OF THE SYNTHETIC POLYPEPTIDE PSH3-INDUCED ANTI-IDIOTYPE ANTIBODY WITH THE INTACT IgM-RF (Sie) ANTIBODY MOLECULE[a]

| Serum Dilution | Absorbance Values at 405 nanometers ($\times 10^3$) | | | |
|---|---|---|---|---|
| | $10^{-3}$ | $10^{-4}$ | $10^{-5}$ | Control |
| Normal Rabbit[b] | 35 | 13 | 3 | 14 |
| Immune Rabbit 1[b] | 292 | 106 | 47 | 46 |
| Immune Rabbit 2[b] | 307 | 164 | 75 | 0 |
| Normal Rabbit[c] | 96 | 19 | 3 | 14 |
| Immune Rabbit 1[c] | 1041 | 376 | 78 | 14 |
| Immune Rabbit 2[c] | 824 | 380 | 75 | 9 |

[a]The solid phase ELISA was performed as in Table 3, except that the wells were coated with 10 micrograms intact IgM-RF per milliliter BBS. The absorbance value readings at 405 nanometers were taken after maintenance of the solid/liquid phase admixture for a time period of one hour (one hour incubation) at room temperature (23° C.), and again after overnight maintenace (incubation) at 4° C.
[b]Data obtained after incubation (maintenance of the solid/liquid phase admixture) for a time period of one hour at room temperature (about 23° C.)
[c]Data obtained after incubation (maintenance of the solid/liquid phase admixture) for a time period of about 18 hours (overnight) at a temperature of 4° C.

Several IgM-RF paraproteins, including IgM-RF (Sie), have been shown to interact with rabbit IgG. Kunkel et al., J. Exp. Med., 137, 331 (1973). Hence, it was necessary to show that the interaction between the anti-polypeptide antibody and the IgM-RF (Sie) was due to the specific binding activity of the anti-polypeptide antibody, and not to a non-specific interaction of the IgM-RF with rabbit IgG in the antisera. Table 5 shows that the anti-polypeptide antibody bound significantly to isolated heavy chains prepared from IgM-RF (Sie), which lacked detectable ability to bind rabbit IgG.

TABLE 5
REACTIVITY OF THE POLYPEPTIDE PSH3-INDUCED ANTI-IDIOTYPE ANTIBODY WITH THE ISOLATED HEAVY CHAIN OF IgM-RF (Sie)[a]

| Serum Dilution | Absorbance Values at 405 nanometers ($\times 10^3$) | | | |
|---|---|---|---|---|
| | $10^{-3}$ | $10^{-4}$ | $10^{-5}$ | Control |
| Normal Rabbit[b] | 16 | 9 | 3 | 10 |
| Immune Rabbit 1[b] | 437 | 105 | 10 | 11 |
| Immune Rabbit 2[b] | 324 | 92 | 6 | 0 |
| Normal Rabbit | 40 | 13 | 4 | 11 |
| Immune Rabbit 1 | 1443 | 404 | 67 | 12 |
| Immune Rabbit 1 | 1084 | 319 | 50 | 5 |

[a]In this determination, the wells were coated with isolated heavy chain of the IgM-RF (Sie) protein (10 micrograms protein per milliliter BBS). Otherwise, the conditions were the same as those described for the assay shown in Table 3.
[b,c]Data were obtained as described in notes b and c of Table 4.

Morever, the F(ab')$_2$ fragments of the anti-polypeptide antibodies, but not those of normal rabbit IgG, bound to the intact IgM-RF (Sie) protein. The results of that binding study are illustrated by the data in Table 6, hereinafter.

TABLE 6
BINDING ACTIVITY OF F(ab')$_2$ INDUCED BY SYNTHETIC PSH3[a]

| Sample: | Absorbance Values at 405 nanometers ($\times 10^3$) to: | | |
|---|---|---|---|
| | BSA | Polypeptide | IgM-Rf (Sie) |
| Original | 17 | 1900 | 587 |
| Effluent | 33 | 374 | 47 |
| Eluate | 28 | 1900 | 459 |
| Normal Rabbit IgG | 59 | 136 | 89 |

[a]In this study, crude F(ab')$_2$ fragments (200 milligrams) of the synthetic polypeptide-induced anti-idiotypic antibodies were added to a 3 milliliter PSH3 peptide-coupled column prepared from cyanogen bromide-activated Sepharose 4B as the solid phase (5 mg/ml gel). After incubation of the solid/liquid phase admixture so formed for 15 minutes at room temperature (23° C.), the effluent was collected. The column was washed the bound material was eluted with 0.1 molar glycine-HCl (pH 3), and the eluate was neutralized. All samples were assayed at a concentration of 25 ug/ml using microtiter wells coated with BSA, the synthetic polypeptide PSH3, or intact IgM-RF (Sie) in the standard ELISA procedure as described before.

The Induced Anti-Peptide Antibody Recognizes A PSH3 Peptide-Determined Epitope on IgM-RF (Sie)

Figure 1:
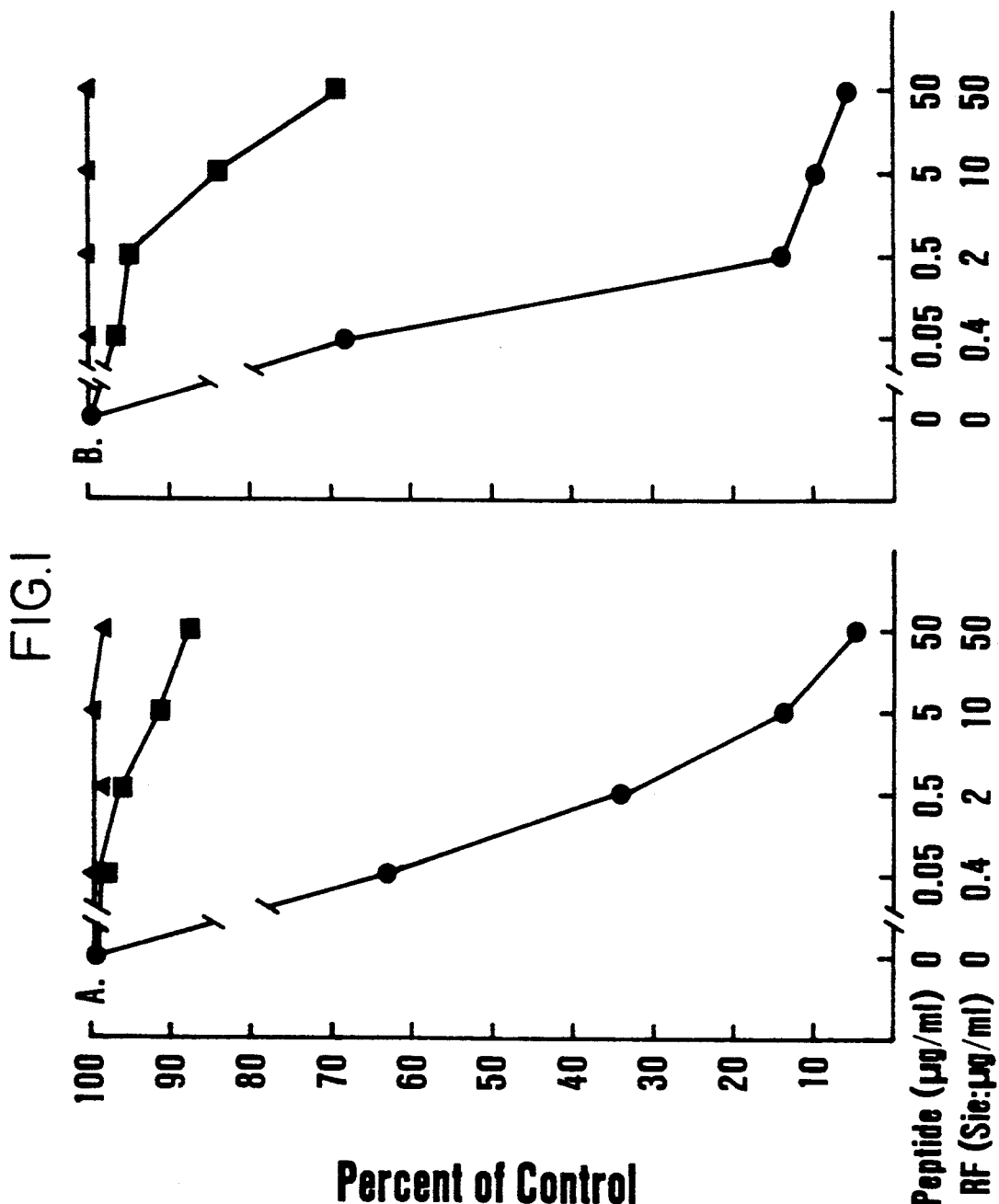
FIG. 1 contains two graphs that illustrate the inhibition of the synthetic polypeptide-induced anti-idiotypic antibody binding to the synthetic polypeptide (A) and to the intact IgM-RF (Sie; B).

To show that the antibody bound to a specific PSH3 polypeptide-determined epitope on the intact IgM-RF (Sie) molecule, an idiotypic antigenic determinant of the immunoglobulin, two types of studies were performed. First, as shown in Table 6, before, most of the IgM-RF (Sie) binding activity was adsorbed by, and eluted from, a synthetic PSH3 polypeptide-coupled immunoadsorbent column. Second, the antibody binding activity to IgM-RF (Sie)-coated plates was inhibited completely by the free synthetic polypeptide PSH3 that substantially immunologically corresponds to an amino acid residue sequence of an idiotypic antigenic determinant of the immunoglobulin in solution (FIG. 1). Under the same inhibiting conditions, a synthetic control polypeptide corresponding to the third hypervariable region of the heavy chain of the monoclonal IgM-RF (Wol) (PWH3), an idiotypic antigenic determinant of another IgM-RF immunoglobulin, did not have significant inhibitory activity, even at a 1,000-fold higher concentration.

The Anti-polypeptide Antibody Recognizes a Private Idiotope in IgM-RF (Sie)

The observation that the anti-polypeptide PSH3 antibody bound efficiently to isolated IgM-RF (Sie) heavy chains enabled development of a sensitive protein blotting method for the detection of the epitope-bearing IgM-RF that avoided non-specific interactions between human IgM-RF and rabbit IgG. A panel of IgM-RF paraproteins, as well as pooled human IgG (Cohn Fraction II), were fractioned by SDS polyacrylamide gel electrophoresis (SDS-PAGE) under reducing conditions, and were then transferred onto nitrocellulose paper, as is known. Autoradiographs were prepared after admixture and incubation with the anti-polypeptide PSH3 antibody, and final development with $^{125}$I-labeled protein-A.

FIG. 2 shows that the anti-polypeptide antibody reacted with the heavy chain of IgM-RF paraproteins, two of which (Glo and The) react with a monoclonal antibody against a cross-reactive (public) idiotype on the Sie molecule. [Carson et al., Mol. Immunol., 20, 1081 (1983)].

Notably, the anti-polypeptide PSH3 antibody did not react detectably with the heavy chains of pooled human IgG.

These results demonstrate that the anti-polypeptide PSH3 antibody, an exemplary antibody of the present invention, recognizes a private idiotype on the heavy chain of IgM-RF (Sie).

Polypeptide-Induced Antibodies Recognize Public Idiotypes of Human RFs

Two rabbits were given two subcutaneous injections of the PSL2 polypeptide PSL2-KLH conjugates and one injection of the PSL2 polypeptide cross-linked with glutaraldehyde, i.e., a synthetic polypeptide that substantially immunologically corresponded to an amino acid residue sequence of an idiotypic antigenic determinant of an immunoglobulin. Sera were obtained one week after the last injection and were analyzed for anti-polypeptide activity by the herein described ELISA technique.

As shown in Table 7, both immune sera contained high titers of anti-PSL2 antibodies. Sera pooled from normal rabbits did not bind significantly to the polypeptide-coated plates. In addition, the immune sera did not react with synthetic polypeptide PSH3, which was used as a control.

Thereafter, the anti-polypeptide antisera were assayed for reactivity with IgM-RF Sie. Table 7 also shows that both antisera, but not the control sera, reacted specifically with the intact antibody molecules. However, the reactivities of both antisera with IgM-RF Sie were relatively weak. This suggests that either only a small fraction of PSL2-induced antibodies reacted with the intact immunoglobulin, or that the interactions between the PSL2-induced antibodies and the IgM-RF Sie were of very low affinity.

TABLE 7

INDUCTION OF ANTI-RF ANTIBODIES WITH SYNTHETIC POLYPEPTIDE PSL2

| | Absorbance Valves at 405 nanometers ($\times 10^3$) | | | |
|---|---|---|---|---|
| | Serum Dilution | | | |
| | $10^{-3}$ | $10^{-4}$ | $10^{-5}$ | Control |
| Polypeptide (PSL2) Antigen[a,b] | | | | |
| Normal Rabbit | 23 | 6 | 3 | 4 |
| Immune Rabbit 1 | 1036 | 302 | 53 | 15 |
| Immune Rabbit 2 | 948 | 370 | 54 | 1 |
| RF (IgM-RF Sie) Antigen[b,c] | | | | |
| Normal Rabbit | 35 | 13 | 3 | 4 |
| Immune Rabbit 1 | 136 | 28 | 5 | 12 |
| Immune Rabbit 2 | 92 | 21 | 13 | 14 |

[a]The synthetic PSL2 polypeptide-induced anti-idiotypic antibody activities were assayed by a solid-phase ELISA on a PSL2 polypeptide-coated microtiter plate. Various dilutions of the sera and control (buffer only) were added to wells in duplicate and admixed and maintained (incubated) for a time period of 3 hours at room temperature (23° C.). Subsequently, the bound antibodies were quantitated with the enzyme-conjugated goat anti-rabbit IgG and substrate, as described before
[b]The specificities of both assays were shown by determining that immun sera did not react with the control PSH3 (polypeptide antigen) and the IgM-RF Lay (paraprotein antigen) respectively.
[c]Same as in Note 1 above, except that the wells were coated with the IgM-RF Sie.

Since PSL2 includes an amino acid residue sequence that corresponds to a hypervariable region sequence shared by L chains of two human monoclonal Igm-RFs [Andrews et al., Proc. Natl. Acad. Sci. U.S.A., 78, 3799 (1981)], the reactivity of the PSL2-induced antibody was determined against a panel of human monoclonal RFs. Table 8 shows that PSL2-induced antibodies react with IgM-RFs Sie, Glo, and to a lesser degree with IgM-RF Pom, but not IgM-RF Lay. Again, the binding was extremely weak.

TABLE 8

REACTIVITIES OF PSL2-INDUCED ANTIBODIES WITH CERTAIN HUMAN MONOCLONAL IgM-RFs[a]

| | Absorbance Values at 405 nanometers ($\times 10^3$) | | | |
|---|---|---|---|---|
| | Coating RF | | | |
| Sample | Sie | Glo | Pom | Lay |
| Anti-IgM[b] | 568 | 735 | 859 | 315 |
| Immune serum[c] | | | | |
| Initial bleed | 38[d] | 109 | 23 | 0 |
| Subsequent bleed | 116 | ND[e] | 23 | ND |

[a]Same as in Table 7, except: 1) the listed RFs were coated at 2 micrograms RF per milliliter BBS; 2) immune sera were assayed at the 1:1000 dilution, and the absorbance valves at 405 nanometers were measured after overnight incubation (maintenance of the solid/liquid phase admixture) in a cold room at 6° C.; and 3) the absorbance valves at 405 nanometers of anti-IgM (from the rabbit immunized with IgM-RF Sie) were measured after 1-hour incubation maintenance at room temperature.
[b]Anti-IgM was used to measure the relative quantities of each IgM-RF.
[c]The rabbit (#1) was initially bled one week after the first injection of glutaraldehyde cross-linked PSL2. Subsequently, the rabbit was further boosted with two more injections (one of similarly cross-linked PSL2 and then one of PSL2-KLH conjugates) to increase the anti-RF Sie titer, and bled one month after the injection.
[d]The numbers expressed are absorbance values due to the reacted immune serum after substracting absorbance values due to the control normal rabbit serum.
[e]ND = Not determined.

It had been shown that several human IgM-RF paraproteins reacted with rabbit IgG [Kunkel et al., J. Exp. Med., 139, 129 (1974)]. Hence, it was necessary to show that the interactions between PSL2-induced antibody and those reactive IgM-RFs were due to the specific binding activity of the PSL2-induced antibodies, and not to the non-specific interactions of the human IgM-RFs with rabbit IgG in the antisera.

Thus, the reactivity of the PSL2-induced antibody with the isolated chains of these IgM-RFs was determined by the Western blot method [Towbin et al., Proc. Natl. Acad. Sci. U.S.A., 76, 4350 (1979)]. As shown in FIG. 4(C), the PSL2-induced antibodies reacted equally well with the light (L) chains of IgM-RFs Sie, Glo and The. Due to the extremely small quantity of IgM-RF Teh available, only 1/5 equivalent weight of IgM-RF Teh was used.

Thus, another Western blot was performed to confirm the antibody reactivity with the RF-Teh [FIGS. 4(D) and 4(E)]. One set of samples was reacted with anti-IgM antiserum to show the relative quantities of different RFs [FIG. 4(D)]; and autoradiographs were developed for a 3-day period.

These results demonstrated that PSL2-induced antibodies reacted with RF-Teh. In addition, the antibody reacted very weakly with the L chains of IgM-RF Pom and pooled IgG. However, most importantly, it reacted neither with the L chain of the IgM-RF Lay, nor with the heavy (H) chains of any IgM-RFs. In contrast, PSH3-induced antibodies reacted only with the H chain of the IgM-RF Sie. These results collectively demonstrate that PSL2-induced antibodies recognized a public idiotype on the L chains of some human IgM-RF.

The Structural Correlate of the RF Public Idiotype Defined by the PSL2-Induced Antibodies To show that PSL2-induced antibodies bound to a specific PSL2-determined idiotype on the reactive IgM-RFs, an idiotypic antigenic determinant of the immunoglobulin, inhibitions of the antibody bindings to both intact IgM-RF Sie, and the isolated L chain of IgM-RF Glo by the PSL2 peptide were determined by ELISA. FIG. 5(A) shows that the antibody binding to RF-Sie was completely inhibited by free synthetic PSL2 peptide in solution. The binding was not affected at all by the control synthetic PSH3 peptide at the same concentrations. Moreover, the control polypeptide PSH3 at 5000 ng/ml completely inhibited the bindings of PSH3-induced antibodies to RF-Sie. Thus, these data indicate that the PSL2-induced antibodies recognize a specific PSL2-determined idiotype on the RF-Sie.

Subsequently, isolated L chains were prepared from the IgM-RF Glo. As expected, PSL2-induced antibodies reacted with the L chains of IgM-RF Glo [FIG. 5(B)]. Moreover, the binding was completely inhibited by the free synthetic PSL2 peptide in solution, but not synthetic PSH3 peptide [FIG. 5(B)]. This suggests that the L chains of RF Sie and RF Glo share a homologous second complementarity-determining region (CDR-2), an idiotypic antigenic determinant of the immunoglobulins, and that the L chain CDR-2 is the structural correlate of the RF public idiotype defined by the PSL2-induced antibody.

The Anti-RF Activity Resides in the Anti-PSL2 Peptide Antibody

To further characterize PSL2-induced antibodies, the IgG fraction was prepared from the antiserum having a high titer of anti-RF activity (e.g., the bleeding from immune rabbit #1 one month after one more injection of glutaraldehyde cross-linked polypeptides and another injection of polypeptide-protein conjugates). Then, the IgG preparation was adsorbed with BSA to remove non-specific binding activity, and the specific antibodies were purified by a PSL2-coupled column.

Table 9 shows that anti-RF activities were adsorbed by, and eluted from the PSL2-coupled column, indicating that anti-RF antibodies of the immune sera were induced by the synthetic peptide directly, and not indirectly through some pathways of the immune network.

TABLE 9

ADSORPTION AND ELUTION OF THE ANTI-RF ACTIVITY FROM A PSL2-COUPLED AFFINITY COLUMN[a]

| | Absorbance Values at 405 nanometers (×10³) ELISA Antigens | | |
|---|---|---|---|
| Sample[b] | Bovine Serum Albumin (BSA) | Polypeptide (PSL2) | IgM-RF Sie |
| Original | 24 | 1319 | 303 |
| BSA-adsorbed | 0 | 1214 | 250 |
| BSA, peptide adsorbed | 0 | 38 | 25 |
| Eluate | 12 | 1859 | 730 |
| Eluate (1 microgram/milliliter) | 0 | 1616 | 375 |

[a]An IgG fraction (100 milligrams) of the antiserum was first adsorbed with a 3 ml BSA-coupled column (5 mg/ml gel), and then loaded onto a 3 ml PSL2-coupled column (1.6 mg/ml gel). After incubation for 15 minutes at room temperature (23° C.), the effluent was collected. Subsequently, the column was washed extensively, and the bound material was eluted with 0.1M glycine-HCl at pH 2.5.
[b]Unless indicated otherwise, all samples were used at a concentration of 10 micrograms per milliliter, and were assayed as described with reference to Table 7.

The results shown in Table 10 indicate that the above-described affinity-purified anti-PSL2 antibody reacts strongly with RFs Sie and Glo, but reacts weakly with RF Pom.

TABLE 10

REACTIVITIES OF THE AFFINITY-PURIFIES ANTI-PSL2 ANTIBODIES WITH CERTAIN HUMAN MONOCLONAL IgM-RFs[a]

| | Absorbance Values at 405 nanometers (×10³)[b] ELISA Antigens (RF) | | |
|---|---|---|---|
| Antibody Sample | Sie | Glo | Pom |
| Anti-PSL2 Antibody | 1136 | 1900 | 256 |
| Antibody-depleted Ig | 57 | 393 | 56 |
| Differential binding[c] | 1179 | 1507 | 200 |

[a]The anti-PSL2 antibody (the eluate in Table 8) and the antibody-depleted Ig (the synthetic peptide-adsorbed fraction in Table 9) were assayed for their reactivities with various IgM-RFs, affixed to micograms per well.
[b]The absorbance value at 405 nanometers was determined after overnight incubation (about 18 hours of maintenance) at room temperature (23° C.) as described before.
[c]Differential binding = [(Absorbance value of antibody) − (absorbance value of antibody-depleted immunoglobulin)].

The Anti-peptide Antibody Reacts with Intact Antibody Molecules in their Native Forms To demonstrate that the denatured IgM-RFs coated onto wells as solid phase-affixed antigens were not responsible for interactions with anti-peptide antibodies, it was shown that IgM-FR Sie in liquid phase was still recognized by anti-peptide antibodies. Table 11 shows that enzyme-conjugated IgM-RF Sie (AP-IgM-RF Sie) bound to wells precoated with anti-PSL2 antibodies, but not the robbit IgG depleted of anti-PSL2 antibodies.

TABLE 11

NATIVE IgM-RF SIE (IN THE LIQUID PHASE) REACTS WITH SYNTHETIC PSL2 POLYPEPTIDE-INDUCED ANTI-IDIOTYPE ANTIBODIES COATED ONTO WELLS

| | Absorbance Values at 405 nanonmeters (×10³) Solid Phase Antigen[a] | |
|---|---|---|
| AP-IgM Sie[b] (ug/ml) | Anti-PSL2 peptide antibody | Antibody-depleted Ig |
| 10 | 1763 | 80 |
| 5 | 1057 | 40 |

TABLE 11-continued

NATIVE IgM-RF SIE (IN THE LIQUID PHASE)
REACTS WITH SYNTHETIC PSL2
POLYPEPTIDE-INDUCED
ANTI-IDIOTYPE ANTIBODIES COATED ONTO WELLS

| AP-IgM Sie[b] (ug/ml) | Absorbance Values at 405 nanonmeters (×10³) Solid Phase Antigen[a] | |
|---|---|---|
| | Anti-PSL2 peptide antibody | Antibody-depleted Ig |
| 2.5 | 603 | 22 |

[a]Polypeptide-induced anti-idiotypic antibodies (the eluate of Table 8) and antibody-depleted IgG (the PSL2 peptide-adsorbed IgG of Table 9) at 8 ug/ml were used to coat separate wells to form solid phase antigens.
[b]IgM-RF Sie was labeled with alkaline phosphatase by reaction with glutaraldehyde. Amounts are ug/ml. Ap-IgM-RF Sie of specified concentrations were distributed to wells in duplicate, and the plate was maintained (incubated) for 3 hours at room temperature (23° C.). After washing, the substrate (p-nitrophenyl phosphate) was added to wells, and the absorbance values at 405 nanometers were measured after 1 hour at room temperature (23° C.).

As shown in FIG. 6, the binding of AP-IgM-RF Sie to the bound anti-PSL2 antibodies was specifically inhibited by synthetic PSL2, but not by control synthetic PSH3. That result demonstrates that binding of the intact IgM-RF Sie to anti-PSL2 antibodies is due to the PSL2-determined epitope, and is not due to the RF activity of the antibody. Taken together, these data demonstrate that the anti-PSL2 antibody reacted specifically with the PSL2-determined idiotype on an intact IgM-RF Sie in its native form.

Expression of Two Major Cross-Reactive Idiotypes on Human IgM-RF Light Chains As described hereinbefore, 10 out of 12 of human monoclonal I9M-RFs studied (83%) bear the PSL2-CRI. The results of further studies demonstrating that 13 out of 17 of IgM-RFs (76%) bear the PSL2-CRI are illustrated in Table 12 wherein idiotypic expression of various IgM-RFs is shown.

Nature, 291 29 (1981)]. However, recently, somatic mutations were found on some IgM antibody molecules encoded by the same gene. [Kocher et al., Mol. Immunol., 18, 1027 (1981); Rudikoff et al., Proc. Natl. Acad. Sci. U.S.A., 81, 2162 (1984); Hartman et al., EMBO, 3, 3023 (1984)]. Thus, it is useful to assess the degrees of somatic diversifications on RF light chains, which bear the PSL2-CRI and are very likely to be encoded by a single putative 'V$_k$RF' gene. [Chen et al., J. Immunol., 134, 3281 (1985)].

In addition, the frequencies of somatic mutations are about three times greater in CDRs than in framework regions (FRs) [Tonegawa, Nature, 302, 575 (1983)]; and polypeptides can routinely be sequenced up to the N-terminal fortieth amino acid residue without cleavages and fragment isolations. [Ledford et al., J. Immunol., 131, 1322 (1983); Hunkapiller et al., Nature, 310, 105 (1984)]. Therefore, antibodies were raised to the third CDR of the RF-Sie light chain (L3) which is identical to the germline sequence of the putative V$_k$RF gene. (Chen et al., supra).

The peptide, designated as PSL3 (Table 1), was synthesized, conjugated to KLH, and used to immunize three rabbits. All three rabits produced anti-peptide antibodies when assayed against the synthetic peptide, PSL3, but only one rabbit produced the peptide-induced anti-Sie antibodies that reacted with the immunoglobulin Sie (Table 13, below). These anti-PSL3 antibodies also reacted with the Sie light chains and ther binding to both intact Sie and Sie light chains was inhibited by the synthetic peptide PSL3.

TABLE 13

ELISA OF ANTI-PSL3,
ANTI-PPH2 AND ANTI-PPH3 ANTISERA

Absorbance Values at 405 nanometers (×10³)
Antigens[a]

TABLE 12

THE IDIOTYPE EXPRESSION OF SEVENTEEN
HUMAN MONOCLONAL IgM RHEUMATOID FACTORS

| IgM-RF | Idiotype | | | | | | |
|---|---|---|---|---|---|---|---|
| | PSL2 | PSL3[a] | PSH3 | PWH2 | PWH3 | PPH2 | PPH3 |
| 1. Cur | ++ | ++ | — | — | — | — | — |
| 2. Gar | ++ | ++ | — | — | — | — | — |
| 3. Gio | ++ | ++ | — | — | — | — | — |
| 4. Got | ++ | ++ | — | — | — | — | — |
| 5. Neu | ++ | + | — | — | — | — | — |
| 6. Pal | ++ | ++ | — | ND | ND | ND | ND |
| 7. Pay | ++ | ++ | — | — | — | — | — |
| 8. Pom | — | — | — | — | — | — | — |
| 9. Sie | ++ | ++ | ++ | — | — | — | — |
| 10. Wol | ++ | — | — | ++ | ++ | — | — |
| 11. Boc | ++ | ++ | — | — | — | — | — |
| 12. Flo | ++ | ++ | — | — | — | — | — |
| 13. Gal | — | ++ | + | — | — | — | — |
| 14. Lew | ++ | — | — | — | — | — | — |
| 15. She | — | — | — | — | — | — | — |
| 16. Lay | — | — | — | ND | ND | — | — |
| 17. Teh | ++ | ND[b] | — | ND | ND | ND | ND |
| Total Positive | 13 | 11 | 2 | 1 | 1 | 1 | 1 |
| Total Assayed | 17 | 16 | 17 | 14 | 14 | 15 | 15 |
| % Positive | 7 | 76 | 69 | 12 | 7 | 7 | 7 |

[a]FIG. 7a (left panel) shows that anti-PSL2 antibodies react with three out of five IgM-RFs in addition to IgM-RF Sie. Together with previous data, 13 out of 17 studied (or 76%) IgM-RFs the '65%' of IgM-RFs that bear the Wa-CRI [Kunkel et al., J. Exp. Med. 137 331, 973 (1973); Kunkel et al., Ann. N.Y. Acad. Sci. 418 324, (1983)] and thus lends further support to the hypothesis that the second CDR on RF light chains (L2) is the structural basis of the Wa-CRI.
[b]ND = Not Determined.

Expression of the PSL3 CRI

It has been suggested that somatic mutuations of Ig may be linked to the Ig class switch [Gearhart et al.,

| Antisera[b] | BSA | Peptide | RF | Iso. Chains |
|---|---|---|---|---|
| Anti-PSL3 | 3 | 836 | 309 | ND |

TABLE 13-continued

ELISA OF ANTI-PSL3, ANTI-PPH2 AND ANTI-PPH3 ANTISERA

| Antisera[b] | Absorbance Values at 405 nanometers (×10³) Antigens[a] | | | |
|---|---|---|---|---|
| | BSA | Peptide | RF | Iso. Chains |
| NRS | 7 | 26 | 151 | ND |
| Anti-PPH2 | 3 | 901 | 66 | ND |
| Anti-PPH3 | 10 | 1,052 | 181 | ND |
| NRS | 0 | 1 | 26 | ND |
| Buffer | 9 | 15 | 13 | ND |
| Anti-PPH2 | 16 | 879 | ND | 79 |
| Anti-PPH3 | 3 | 947 | ND | 398 |
| NRS | 0 | 10 | ND | 35 |

[a]Antigens were affixed to microtiter plate wells as a solid phase at the following concentrations; peptide and RF at 2 ug/ml; BSA at 1 mg/ml; and the isolated Pom heavy chains at 10 ug/ml. Synthetic peptides and RFs used were those relevant to the antiserum used; i.e, PSL3, PPH2, or PPH3; and Sie or Pom.
[b]Antisera were used at 1:100 dilution. NRS is normal rabbit serum.

The immunoreactivity of anti-PSL3 antibodies against a panel of 16 human monoclonal IgM-RFs was analyzed by immunoblotting. FIG. 8 shows that anti-PSL3 reacts with only two out of three Wa-CRI positive RFs, indicating that the third CDR of the light chain is unlikely to be the structural basis of the Wa-CRI. FIGS. 7b (right panel) and 9 show that anti-PSL3 reacts with three additional RFs, but with none of six Bence-Jones proteins. As described in relation to Table 12, anti-PSL3 defines a new RF-associated CRI, an idiotypic antigenic determinant, expressed by about 69% of the IgM-RFs studied.

Expression of Three Heavy Chain Idiotypes Associated with Two Wa-CRI Positive IgM-RFs A similar strategy to that described before was used to study the idiotypes associated with the RF heavy chains. Four synthetic peptides having amino acid residue sequences substantially immunologically corresponding to the amino acid residue sequences of second and third CDR of the Sie and Wol heavy chain idiotypic antigenic determinants of the immunoglobulins were prepared and used to innmunize rabbits. Sera from both PSH2-immunized rabbits reacted only with synthetic peptide, but not with the Sie immunoglobulin or isolated Sie heavy chains, in either ELISA or immunoblotting.

In contrast, anti-PSH3 from all four immunized rabbits reacted specifically with both Sie and isolated Sie heavy chains as shown in FIGS. 10 and 11c (lower left panel). When screened against the same 17 IgM-RFs shown in Table 12, only one RF (IgM-RF Gal) was weakly positive, in addition to Sie.

Each of PWH2 and PWH3 synthetic peptides was used to immunize two rabbits, and all sera reacted weakly with the isolated heavy chains of Wol. FIGS. 11d (lower right panel) and 12 and 13 show that immunoreaction was positive only with Wol among 14 IgM-RFs analyzed. In addition, anti-PWH3 reacted surprisingly with the isolated Sie light chains. This binding is considered non-specific.

Expression of Two Heavy Chain Idiotypes Associated with the Po-CRI Positive RFs

Compared with the Wa-CRI, the Po-CRI positive RFs contain only 20% of the human monoclonal IgM-RFs. [Kunkel et al., J. Exp. Med., 137, 331 (1973)]. The variable regions of two Po-CRI positive RFs had been sequenced and were found to share homologous heavy chains. [Capra et al., Proc. Natl. Acad. Sci. U.S.A., 71, 4032 (1974); Klapper et al., Ann. Immunol. (Inst. Pastuer), 127c, 261 (1976)]. Importantly, they shared identical second and third CDRs on heavy chains (H2 and H3).

Peptides corresponding to the two identified idiotypic antigenic determinant regions were synthesized (Polypeptides PPH3 and PPH2, Table 1), and were used to immunize rabbits. Both PPH3-immunized rabbits and one of two PPH2-immunized rabbits produced antibodies reactive with the parent protein Pom (Table 13). FIGS. 11 (a and b, upper panel) and 14 show that anti-PPH2 and anti-PPH3 antibodies reacted only with Pom heavy chains, among a total of 15 RFs analyzed.

The reactivities of both anti-PPH2 and anti-PPH3 toward RF-Lay were analyzed by ELISA and immunoblotting. The result was surprisingly negative.

The reason for the observed lack of immunoreactivity is unknown. The lack of reaction may be due to 1) the amino acid sequence of Lay heavy chain being incorrect; 2) the Lay protein used might have been different from the Lay used in sequencing (i.e., they were prepared from different plasma samples which were obtained from the same patients at different times); and 3) the different amino acid residues outside CDR2 and CDR3 may affect the mobilities and accessibilities of these two CDRs, and thus hinder their interactions with the antibodies. It is noted that some sequence differences were recently found between two IgM-RF samples which were obtained three years apart from a patient.

Production of Anti-Peptide Antibodies For Additional Studies

The sequences of the synthetic peptides used in additional studies including two additional peptides that had not previously been studied and are each related to the first CDR of an IgM-RF are listed in Table 14.

TABLE 14

AMINO ACID SEQUENCES OF PEPTIDES[a]

| Name | Protein | Residue No.[b] | Amino Aicd Sequence |
|---|---|---|---|
| 1 PPH1 | Pom | 22–35 | AASGFTFSSSAMSC[c] |
| 2 PPH2 | Pom | 49–65 | AWKYENGNDKHYADSVNG(GGC)[d] |
| 3 PPH3 | Pom | 95–102 | DAGPYVSPTFFAH(GGC)[d] |
| 4 PSH1 | Sie | 22–35 | KTSGGTFSGYTISC[e] |
| 5 PSH2 | Sie | 49–65 | GSPAKWTDPFQGVYIKWE(GGC)[e] |
| 6 PSH3 | Sie | 95–102 | EWKGQVNVNPFDY(GGC)[e] |
| 7 PWH2 | Wol | 49–65 | GQIPLRFNGEVKNPGSVV(GGC)[e] |
| 8 PWH3 | Wol | 95–102 | EYGFDTSDYYYYY(GGC)[e] |

[a]The abbreviations are as described in Table 1.
[b]Numbering is after Kabat et al., U.S. Dept. of Health and Human Service, (1983).
[c]Sequences reported by Capra et al., Proc. Natl. Acad. Sci. USA, 71, 4032 (1974).
[d]Sequences reported by Andrews et al., Proc. Natl Acas. Sci. USA, 78, 3799 (1981).

Antibodies against each peptide-KLH conjugate were prepared in at least two rabbits that were bled bi-weekly. All serum specimens were tested by ELISA as described herein for peptide binding activity. FIG. 15 demonstrates that, in each case, high titers of anti-peptide antibodies were elicited. None of the antibodies bound significantly to an irrelevant peptide (PWL3). Pooled serum from non-immune rabbits did not react substantially with the peptide-coated plates. Thus, all the peptides studied were immunogenic as used. There was no apparent correlation between the sequence of the CDR peptide and the degree of immunogenicity.

Reactivity of Anti-Peptide Antisera by Immunoblotting

The reactivity of the anti-peptide antisera elicited by the peptides of Table 14 with isolated heavy chains of IgM-RFs was analyzed by immunoblotting as described in detail herein. The results are summarized in Table 15.

TABLE 15
REACTIVITY OF ANTI-PEPTIDE ANTIBODIES WITH A PANEL OF HUMAN IgM-RF[a] BY IMMUNOBLOTTING[b]

| ANTIPEPTIDE ANTISERUM | IgM-RF Antigen | | | | | | | | | | | | | | | |
|---|---|---|---|---|---|---|---|---|---|---|---|---|---|---|---|---|
| | Pom | Sie | Wol | Les | Pay | Got | Glo | Neu | Neu | Cha | Sou | Mcd | Ark | Tal | Bel | Dri | Blo |
| PPH1 | + | − | − | − | − | − | − | − | − | − | − | − | − | − | − | − | − |
| PPH2 | + | − | − | − | − | − | − | − | − | − | − | − | − | − | − | − | − |
| PPH3 | + | − | − | − | − | − | − | − | − | − | − | − | − | − | − | − | − |
| PSH1 | − | − | − | − | − | − | − | − | − | − | − | − | − | − | − | − | − |
| PSH2 | − | − | − | − | − | − | − | − | − | − | − | − | − | − | − | − | − |
| PSH3 | − | + | − | − | − | − | − | − | − | − | − | − | − | − | − | − | − |
| PWH2 | − | − | + | − | − | − | − | − | − | − | − | − | − | − | − | − | − |
| PWH3 | − | − | + | − | − | − | − | − | − | − | − | − | − | − | − | − | − |

[a]The IgM-RFs Pom, Sie, Wol, Pay, Got, Glo, Neu and Gar have been described in Ledford et al., J. Immunol., 131, 1322 (1983).
[b]A (+) denotes reactivity of the antipeptide antibody with the RF, as detected by immunoblotting. A (−) indicates lack of reactivity.

There are at least two points to be noted from Table 15. First, no antiserum reacted with more than a single RF. Second, not all antisera reacted even with the isolated heavy chain of the RF containing the immunizing sequence. Specifically, the anti-PSH1 and anti-PSH2 antisera failed to bind top isolated Sie heavy chains. This has been a consistent result, despite repeated immunizations in several rabbits.

In every case, synthetic peptide-induced antisera directed against the third CDR sequence reacted more strongly with the isolated heavy chains than did antisera directed against the first or second CDR. This result is illustrated in FIG. 16, which compares the reactivity of each anti-peptide antiserum with its respective RF heavy chain. Although anti-PPH1 and anti-PWH2 appear to be unreactive in this Figure they were in fact shown to be reactive with longer times of exposure.

Binding of Anti-Peptide Antisera To Intact RF by ELISA

The binding of each of the eight different anti-peptide antibodies induced by the peptides listed in Table 14 to intact IgM-RF was tested by ELISA, as described in detail hereinafter, using increasing concentrations of anti-peptide antisera and microtiter plates coated with the purified RF proteins as antigen-affixed solid supports (FIG. 17). All three anti-CDR 3 antisera (induced by PPH3, PSH3 and PWH3) bound to the intact IgM-RF molecule. In contrast, of the five antibodies against CDR 1 and CDR 2 peptides (induced by PPH1, PPH2, PSH1, PSH2 and PWH2), only anti-PPH2 reacts well with the corresponding IgM-RF protein. As noted earlier (FIG. 15), all eight antisera were high titer and specifically recognized the immunizing CDR peptide Induction of Anti-RF Antibody With the PGL1 Peptide Three rabbits were inoculated with two subcutaneous injections of the PGL1 peptide conjugated to KLH as an immunogen, and their sera were analyzed for anti-peptide antibody activity by ELISA as described in detail herein. All three immunized rabbits produced anti-PGL1 antibody. Antisera drawn from a rabbit on two different days reacted significantly with the corresponding intact IgM-RF Glo (see Table 16).

TABLE 16
INDUCTION OF ANTI-RF ANTIBODIES WITH PGL1 PEPTIDE[a]

| | Binding to antigens ($A_{405} \times 10^3$) | | |
|---|---|---|---|
| Samples | PSH3 | PGL1 | Glo |
| Buffer only | 24 | 14 | — |
| Normal | 111 | 80 | 315 |
| Immune 1 | — | — | 448 |
| Immune 2 | 98 | 1,468 | 449 |

[a]A rabbit was immunized with PGL1-KLH in CFA on days 0, 30, and 120, and was bled on day 70 (Immune 1) and day 135 (Immune 2). The antisera were assayed at 1:1000 dilution following the ELISA techniques described previously.

Since IgM-RF Glo reacted with rabbit IgG, which substantially immunologically corresponds to human IgG, an immunoblot assay was used to demonstrate the de facto anti-idiotype activity of the anti-PGL1 antiserum. [Chen et al., Proc. Natl. Acad. Sci. U.S.A., 81, 1784 (1984)].

Briefly, IgM-RF Glo and the control, pooled human IgG (Cohn fraction II), were fractionated by electrophoresis under reducing conditions, and then transferred onto nitrocellulose paper. After incubation with the anti-peptide antibody and final development with $^{125}$I-labeled protein A, autoradiographs were prepared FIG. 18 shows that the anti-PGL1 antiserum reacts with the kappa light chain of Glo, but not with the heavy chain of Glo, nor with the light chains of pooled human IgG. Thus, the anti-PGL1 antiserum reacts with the kappa light chain of Glo, but not with the heavy chain of Glo, nor with the light chains of pooled human IgG. Thus, the anti-PGL1 di splays anti-idiotype activity.

Subsequently, the specificity of the anti-PGL1 antiserum against a panel of human IgM-RF was examined by the immunoblot method. FIG. 19 shows that anti-PGL1 antibody reacts well with IgM-RF proteins Gar, Glo, Got, and Pal, very weakly with Neu and Pay, and not at all with IgM-RF Lay. A weak reaction was separately shown with IgM-RF Sie.

Except for IgM-RF Pal, the amino acid sequences of the first CDR of the Kappa chains of these IgM-RF have been reported [Capra et al., *Adv. Immunol.*, 20 1 (1975); Ledford et al., *J. Immunol.*, 131, 1322 (1983): Klapper et al., *Ann. Immunol.* (Paris), 127c, 261 (1976); and Andrews et al., *Proc. Natl. Acad. Sci. U.S.A.*, 78, 3799 (1981)] and are shown in Table 17.

intact IgG molecules, and that anti-PGL1 antiserum contains both epibody and anti-gamma antibody that was indirectly induced.

A summary of those binding and inhibition studies with anti-PGL1 antiserum is shown in Table 18, below.

TABLE 17

AMINO ACID SEQUENCES OF THE KAPPA CHAINS OF HUMAN MONOCLONAL IgM-RF PARAPROTEINS IN THE FIRST CDR

| IgM-RF | ID[a] | 24 | 25 | 26 | 27 | 27A | 28 | 29 | 30 | 31 | 32 | 33 | 34 |
|---|---|---|---|---|---|---|---|---|---|---|---|---|---|
| Glo[c] | + | Arg | Ala | Ser | Gln | Ser | Val | Ser | Ser | Ser | Tyr | Leu | Ala |
| Gar[c] | + | — | — | — | — | — | — | — | — | — | — | — | — |
| Got[d] | + | — | — | — | — | — | — | Arg | — | — | — | — | — |
| Lay[e] | — | Gln | — | — | — | ( ) | Asn | Val | Asn | Ala | — | — | Asn |
| Neu[d] | ± | — | — | — | — | — | — | — | — | Arg | — | — | — |
| Pay[d] | ± | — | — | — | — | — | Lys | — | — | — | — | — | — |
| Sie[f] | ± | — | — | — | — | — | — | — | Asn | — | — | — | — |

[a]Reactivity with anti-PGL1. "+" indicates the RF reacted well. "±" indicates very weak reaction. "—" indicated no reaction. See also FIG. 19.
[b]Residue number according to Kabat et al. Sequence of Proteins of Immunological Interest, Dept. of Health and Human Services (1983).
[c]Amino acid sequence were reported by Capra et al., Adv. Immunol., 20, 1 (1975).
[d]Amino acid sequences were reported by Ledford et al., J. Immunol., 131, 1322 (1983).
[e]Amino acid sequences were reported by Klapper et al., Ann Immunol. (Paris), 1237C, 261 (1976).
[f]Amino acid sequences were reported by Andrews et al., Proc. Natl. Acad. Sci. USA, 78, 3799 (1981).

The results discussed hereinabove and shown in FIGS. 18 and 19 suggest that the majority of the polyclonal anti-PGL1 antibodies recognize a determinant associated with Val-Ser-Ser-Ser (residues 28–31). However, the anti-PGL1 antibodies also react with IgM-RF Got, which has Arg instead of Ser at position 29. One possible explanation for that binding is that the antigenic determinant for the majority of anti-idiotypes is Ser-Ser-Ser, that a lesser fraction recognizes Ser-Ser-Tyr, and that Val serves to enhance the binding of both antibodies through its hydrophobicity. Since both Ser and Tyr share the same functional hydroxyl group, the Ser-Ser-Tyr- and Ser-Ser-Ser-specific antibodies might be expected to have partial cross-reactivity.

Anti-PGL1 Antibody Reacts With Human IgG

The epibody described by Bona et al., *J. Exp. Med.*, 156, 986 (1982), was prepared against human IgM-RF Glo, which contain the PGL1 sequence. As shown in FIG. 18, the PGL1-induced anti-idiotype bound to the isolated gamma chains of human IgG. To assess the structural basis for this cross-reaction, two types of studies were performed.

First, the antibody-binding activity to the gamma chains was inhibited partially by the free PGL1 peptide in solution (FIG. 18). Under the same conditions, an unrelated peptide, PSH3, did not detectably inhibit the reaction. However, it should be noted that the peptide inhibition of antibody binding to IgG gamma chain was not as significant as to Glo light chain, reaching a maximum of 70 percent (as suggested by the intensity of autoradiographs). This suggests that some anti-gamma antibodies might have been induced nonspecifically or indirectly.

Second, the PGL1-induced epibodies were enriched by affinity chromatography on a human IgG column. As shown in FIG. 20, the eluate from the human IgG column reacted with both the Glo light chain and IgG gamma chains, but not with IgG light chains. However, the binding to Glo light chain, but not to IgG gamma chain, was completely inhibited by the PGL1 peptide. Altogether, these results suggest that a portion of PGL1-induced anti-idiotype antibodies reacted with

TABLE 18

THREE COMPONENTS IN THE ANTI-PGL1 ANTISERUM[a]

| | Binding Reactivity with: | | | | |
|---|---|---|---|---|---|
| Antibody | Glo | Glo light | IgG | IgG heavy | PGL1 |
| Anti-Glo, conventional | + | + | — | — | + |
| Epibody | + | — | + | + | + |
| Anti-IgG | — | — | + | + | — |
| | Inhibition of Binding by PGL1[b] | | | | |
| Anti-Glo, conventional | ±[c] | + | NA[d] | NA[d] | + |
| Epibody | ± | + | — | + | + |
| Anti-IgG | NA[d] | NA[d] | — | — | NA[d] |

[a]"+" indicates binding or inhibition, respectively; "—" indicates an absence of binding or inhibition, respectively; and "±" indicates weak binding
[b]Inhibition of binding to intact protein was done by ELISA.
[c]PGL1 at 500 ug/ml gave about 10% inhibition.
[d]Not applicable.

VI. MATERIALS AND METHODS

A. Synthesis of Polypeptides Related to IgM-RF

Ten peptides in addition to PGL1 each having an amino acid residue sequence that substantially corresponds to an amino acid residue sequence of a primary idiotypic antigenic determinant of an IgM-RF paraprotein were synthesized by the solid-phase method, using a Beckman model 990B peptide synthesizer as described in Chen et al., *Proc. Natl. Acad. Sci. U.S.A.*, 81 1784 (1984).

Briefly, 1.00 gram (g) (about 0.5 milliequivalent) of N-t-butoxycarbonylglutamic acid (BocGlu) linked to a cross-linked polystyrene resin was used along with the following side-chain protecting groups: O-bromobenzyl-oxycarbonyl for tyrosine and lysine; O-benzyl for glutamic acid, threonine, serine and aspartic acid; S-methoxybenzyl for cysteine.

Protected amino acids were recrystallized from appropriate solvents to give single spots by thin-layer chromatography. All couplings were carried out with a 10-fold excess of protected amino acid plus dicyclohexylcarbodiimide. For asparagine and glutamine, an equal molar amount of N-hydroxybenzotriazole was added to the protected amino acid and dimethylformamide was used as the solvent.

All coupling reactions were 99% complete by the picric acid test. The protected peptide-resins so formed were treated with twice their weight of anisole and 40 times their volume relative to weight with anhydrous hydrogen fluoride at 4° C. for 1 hour. After the hydrogen fluoride was evaporated with a stream of $N_2$, the peptide was extracted with anhydrous ether three times, filtered, and dried in vacuo. The amino acid analyses of the peptides were typically within 5% of theory.

B. Antibody Production with IgM-RF Related Polypeptides

1. Immunizations

The synthetic polypeptides described in Section VI(A) were reacted in separate reactions via their terminal cysteines to keyhole limpet hemocyanin (KLH) as an antigenic carrier with m-maleimidobenzoyl N-hydroxysuccinamide ester to form conjugates, as described in Green et al., *Cell*, 28, 477 (1982) and Liu et al., *Biochemistry*, 18, 690 (1979).

For the most part, rabbits were immunized twice with conjugates emulsified in complete Freund's adjuvant (CFA) and then were boosted twice with glutaraldehyde cross-linked peptides in incomplete Freund's adjuvant (IFA), as described hereinbelow.

Briefly, each of two rabbits was injected subcutaneously with 2.5 mg (milligrams) of a synthetic peptide conjugate emulsified in CFA. The injection was repeated two months later. Three weeks after the second immunization, the rabbits were boosted again with 2.5 mg of glutaraldehyde cross-linked polypeptide in IFA. The latter reagent was prepared by the addition of glutaraldehyde (final concentration 0.25% v/v) to a 5 milligrams per milliliter (mg/ml) solution of polypeptide in isotonic phosphate-buffered saline, followed by 1-hour incubation at room temperature, and recovery of the cross-linked product. The rabbits were bled, and the antisera were stored at −20° C. until analyzed.

Thereafter, the antisera were obtained and were characterized. The immunization protocol was later modified to two immunizations of conjugates in CFA at one-month intervals. This protocol generated similar results to an earlier protocol described above.

2. Purification of Proteins

Plasma or purified proteins from patients with monoclonal IgM cryoglobulins were purified by repeated precipitation at 4° C., followed by chromatography on Sephadex G-200 (Pharmacia Fine Chemicals, Piscataway, N.J.) or Ultrogel AcA 22 (LKB Instruments, Rockville, Md.) in 0.2 molar sodium acetate at pH 3.5. IgM and IgG peaks were identified by immunodiffusion, and then the appropriate fractions were pooled, and were stored at a temperature of −20° C. Human IgG was prepared from Cohn fraction II (Sigma, St. Louis, Mo.) by DEAE cellulose chromatography in 0.01 molar sodium phosphate at pH 8.0.

The heavy and light chains of the IgM-RF proteins Sie, Wol, and Pom were separated on a Sephadex G-100 (Pharmacia Fine Chemicals) column with 1 molar acetic acid, after complete reduction and alkylation as reported by Bridges et al., *Biochemistry*, 10, 2525 (1971). The separated light and heavy chains were stored frozen at a concentration of 1 mg/ml. Using a radioimmunoassay specific for IgM heavy chains or kappa light chains, it was estimated that the heavy chains contained less than 5% light chains, while the light chains contained less that 2% heavy chains.

3. Enzyme Linked Immunosorbent Assay (ELISA)

The synthetic polypeptide [100 micrograms per milliliter (ug/ml)], various purified monoclonal IgM-RF (10 ug/ml), and isolated heavy and light chains from the IgM-RF proteins (10 ug/ml) were dissolved in borate-buffered saline (BBS) including 0.1 molar borate and 0.2 molar NaCl at pH 8.2. The resulting admixture was then added to wells of polyvinyl chloride microtiter plates (Costar #3590) at a concentration of about 100 microliters per well.

After maintaining the admixture for a time period of about 18 hours (overnight) at 4° C., the plates were washed twice with BBS containing 0.5% Tween-20 [polyoxyethylene (20) monolaurate (#P-1379 Sigma Chemical Co., St. Louis, Mo.); BBS/Tween-20] and were quenched with BBS containing 1% bovine serum albumin (BSA) for one hour at room temperature to form solid phase-affixed antigens. Then, 100 microliters (ul) of serum diluted with BBS containing 0.5% BSA (BBS/0.5% BSA) were distributed to the wells in duplicate to form solid/liquid phase admixtures.

The plates were incubated (maintained) for 3 hours at room temperature. Subsequently, the solid and liquid phases were separated and each well was washed 3 times with BBS/Tween-20. Then, 100 ul aliquots of a 1:800 dilution of alkaline-phosphatase labeled goat anti-rabbit IgG (Kirkegaard and Perry, Gaithersburg, Md.) that had been previously adsorbed with human IgG-Sepharose 4B (Sepharose 4B is a product of Pharmacia Fine Chemicals) were dispensed to each of the wells to form a second solid/liquid phase admixture.

After another one hour incubation (maintenance of the admixture) at room temperature, the phases were separated and the plates were washed 5 times with BBS/Tween-20. Thereafter, 100 ul of p-nitrophenyl phosphate (1 mg/ml) in 0.05 molar sodium carbonate pH 9.8 was added to the wells, and the absorbance values at 405 nanometers (nm) were measured in a Titertek Multiscan spectrophotometer after a time period of one hour at room temperature, or 16 hours at 4° C.

4 Inhibition Assay

The inhibition of the anti-polypeptide antibody binding to plates coated with IgM-RF (for example, Sie) or the polypeptide (for example, PSH3) as solid phase-affixed antigens were assessed by the previously described ELISA methods, but with the following modifications. The antiserum diluted 1:1,000 in BBS/0.5% BSA, was first admixed with an equal volume of inhibitor (e.g., Sie, immunizing polypeptide PSH3, or control unrelated polypeptide, for example, PWH3) at the concentration specified in the relevant Figures, and then was distributed to wells in duplicate 100 ul aliquots to frozen solid/liquid phase admixtures.

5. Adsorption and Elution of the IqM-RF (Sie)-binding activity

The globulin fraction of anti-polypeptide antisera was precipitated twice with 40% ammonium sulfate, and then was digested with 3% (w/w) pepsin for 16 hours at 37° C and pH 4.1 to form F(ab')$_2$ antibody portions (fragments). After neutralization, the digest was recirculated over a protein-A Sepharose 4B column (Pharmacia Fine Chemicals, Piscattaway, N.J.) to remove undigested IgG. Subsequently, the F(ab')$_2$ fragments were recirculated over a synthetic polypeptide-coupled Sepharose 4B affinity column (at about 6.6 mg/ml gel ×5 ml), that had been prepared with cyanogen bromide-activated Sepharose-4B (Sigma, St. Louis, Mo.).

After removal of non-bound material with BBS, the F(ab')₂ anti-polypeptide antibody was eluted with 0.1 molar glycine HCl, pH 3.0, and was then dialyzed against BBS.

6. Protein Blotting

The reactivity of the anti-polypeptide antibody with immunoglobulin light and heavy chain polypeptides was assayed by the Western blot method. [Towbin et al., *Proc. Natl. Acad. Sci. U.S.A.*, 76, 4350 (1979) as modified by Billings, et al., *J. Immunol.*, 128, 1176 (1982)].

Briefly, about 20 ug of individual monoclonal IgM-RF proteins [as discussed in Chen et al., *Proc. Natl. Acad. Sci. U.S.A.*, 81, 1784 (1984)] or pooled human IgG in 25 ul of sample buffer supplemented with 0.01 percent 2-mercaptoethanol, was loaded onto each slot of a 10% polyacrylamide slab gel, containing 0.1% sodium dodecyl sulfate. [Laemelli, *Nature*, 227, 680 (1970)]. After electrophoresis for 3 hours at 30 milliamperes, the proteins in the gel were transferred electrophoretically to nitrocellulose paper.

Protein binding sites on the paper were quenched by contact with a phosphate buffered-saline (PBS) solution containing both BSA (5%) and ovalbumin (5%) for one hour at room temperature. Thereafter, the paper was contacted with a liquid composition containing the anti-polypeptide antiserum (1:100 dilution in PBS containing 2% of both BSA and ovalbumin) for one hour. After washing, the paper was developed with the $^{125}$I-labelled protein A (1 mCi/mg, $2 \times 10^5$ cpm/ml) for another hour. After extensive washing, the paper was dried and finally exposed to XAR-5 film (Eastman Kodak Co., Rochester, N.Y.) overnight at $-70°$ C.

The foregoing is intended as illustrative of the present invention but is not limiting. Numerous variations and modifications can be effected without departing from the spirit and scope of the novel concepts of the invention. It is to be understood that no limitation with respect to the specific antibodies, compositions and uses described herein is intended or should be inferred.

This invention was made with Government support and the Government has certain rights in the invention pursuant to Grants Nos. AM25443 and AG04100 awarded by the National Institute of Health.

What is claimed is:

1. A synthetic polypeptide having an amino acid residue sequence containing about 6 to about 40 amino acid residues immunologically corresponding substantially to a primary amino acid residue sequence of an idiotypic determinant of an immunoglobulin said idiotype determinant including an amino acid residue sequence, taken from left to right and in the direction from amino-terminus to carboxy-terminus, represented by a formula that is a member of the group consisting of
   YGASSRATGIPDR,
   KYSGGTFSGYTISC,
   EWKGOVNVNPFDY, and
   EYGFDTSDYYYYY.

2. The synthetic polypeptide according to claim 1 wherein said synthetic polypeptide contains from about 8 to about 20 amino acid residues.

3. The synthetic polypeptide according to claim 1 wherein a coupling group is attached to one end of said peptide.

4. The synthetic peptide according to claim 3 wherein said coupling group is an amino acid residue of a sequence of amino acid residues selected from coupling groups consisting of C and GGC.

5. The synthetic peptide according to claim 3 wherein the coupling group is attached to the carboxy-terminus end of said synthetic polypeptide.

6. A synthetic polypeptide containing up to about 20 amino acid residues including the sequence of amino acid residues, taken from left to right and in the direction from amino-terminus to carboxy-terminus, represented by the formula UGASSRATGIPDR.

7. A synthetic polypeptide containing up to about 20 amino acid residues including the sequence of amino acid residues, taken from left to right and in the direction from amino-terminus to carboxy-terminus, represented by the formula KTSGGTFSGYTISC.

8. A synthetic polypeptide containing up to about 20 amino acid residues including the sequence of amino acid residues, taken from left to right and in the direction from amino-terminus to carboxy-terminus, represented by the formula EYGFDTSDYYYYY.

9. A synthetic polypeptide containing up to about 20 amino acid residues including the sequence of amino acid residues, taken from left to right and in the direction from amino-terminus to carboxy-terminus, represented by the formula AASGFTFSSSAMSC.

10. A synthetic polypeptide containing up to about 20 amino acid residues including the sequence of amino acid residues, taken from left to right and in the direction from amino-terminus to carboxy-terminus, represented by the formula RASQSVSSSYLA.

11. A synthetic polypeptide containing up to about 20 amino acid residues including the sequence of amino acid residues, taken from left to right and in the direction from amino-terminus to carboxy-terminus, represented by the formula EWKGQVNVNPFDY.

12. A conjugate comprising a synthetic polypeptide bound to an antigenic carrier, said conjugate containing an amount of said synthetic polypeptide sufficient to induce production of antibodies in a host animal when said conjugate is injected into said host animal in an antibody-inducing effective amount in a physiologically tolerable vehicle, and said synthetic polypeptide having an amino acid residue sequence containing about 6 to about 40 amino acid residues immunologically corresponding substantially to a primary amino acid residue sequence of an idiotypic determinant of an immunoglobulin, said idiotype determinant including an amino acid residue sequence, taken from left to right and in the direction from amino-terminus to carboxy-terminus, represented by a formula that is a member of the group consisting of
   YGASSRATGIPDR,
   KTSGGTFSGYTISC,
   EWKGOVNVNPFDY, and
   EYGFDTSDYYYYY.

13. An inoculum comprising in a physiologically tolerable vehicle, an antibody-including effective amount of a synthetic polypeptide having an amino acid residue sequence containing about 6 to about 40 amino acid residues immunologically corresponding substantially to a primary amino acid residue sequence of an idiotypic determinant of an immunoglobulin, said idiotypic determinant including an amino acid residue sequence, taken from left to right and in the direction from amino-terminus to carboxy-terminus, represented by a formula that is a member of the group consisting of
   YGASSRATGIPDR,
   KTSGGTFSGYTISC,
   EWKGOVNVNPFDY, and
   EYGFDTSDYYYYY.

14. The inoculum according to claim 13 wherein said physiologically acceptable vehicle is a member of the group consisting of water, saline, a buffered salt solution, a physiologic sugar solution and an adjuvant.

15. The inoculum according to claim 13 wherein said synthetic polypeptide is bound to a carrier.

16. Antibodies raised in an animal host to a synthetic polypeptide having an amino acid residue sequence containing about 6 to about 40 amino acid residues immunologically corresponding substantially to a primary amino acid residue sequence of an idiotypic determinant of an immunoglobulin, said idiotypic determinant including an amino acid residue sequence, taken from left to right and in the direction from amino-terminus to carboxy-terminus, represented by a formula that is a member of the group consisting of
   YGASSRATGIPDR,
   KTSGGTFSGYTISC,
   EWKGOVNVNPFDY, and
   EYGFDTSDYYYYY,
   said antibodies having the capacity of immunoreacting with said idiotypic determinant.

17. A diagnostic system for assaying for the presence of an idiotypic determinant of an immunoglobulin including an assay-sufficient amount of antibodies raised in an animal host to a synthetic polypeptide having an amino acid residue sequence containing about 6 to about 40 amino acid residues immunologically corresponding substantially to a primary amino acid residue sequence of an idiotypic determinant including an amino acid residue sequence, taken from left to right and in the direction from amino-terminus to carboxy-terminus, represented by a formula that is a member of the group consisting of
   YGASSRATGIPDR,
   KTSGGTFSGYTISC,
   EWKGOVNVNPFDY, and
   EYGFDTSDYYYYY.
   said antibodies having the capacity of immunoreacting with said idiotypic determinant.

18. The diagnostic system according to claim 11 wherein said antibodies are substantially intact antibodies.

19. The diagnostic system according to claim 17 wherein said antibodies are Fab or F(ab')$_2$ portions of antibodies.

20. The diagnostic system according to claim 17 further including an indicating means.

21. The diagnostic system according to claim 20 wherein said indicating means is in a second container and comprises enzyme-linked second antibodies, said second antibodies being raised to antibodies of the same class and from the same species as the first named antibodies, and signalling said immunoreaction by binding to said first named antibodies present in said immunoreactant, said signal being indicated by the reaction of said linked enzyme with an added substrate.

22. The diagnostic system according to claim 20 wherein said indicating means comprises a radioactive element bonded to substantially all of said antibodies.

23. A method of immunoregulating an autoimmune immunoglobulin in a human immune system comprising the steps of:
   (a) providing an inoculum comprising, in a physiologically tolerable vehicle, a synthetic polypeptide having an amino acid residue sequence containing about 6 to about 40 amino acid residues immunologically corresponding substantially to a primary amino acid residue sequence of an idiotypic determinant of an immunoglobulin, said idiotypic determinant including an amino acid residue sequence, taken from left to right and in the direction from amino-terminus to carboxy-terminus, represented by a formula that is a member of the group consisting of
   YGASSRATGIPDR,
   CQQYGSSPQTFG,
   KTSGGTFSGYTISC,
   GSPAKWTDPFQGVYIKWE,
   EWKGQVNVNPFDY,
   GQIPLRFNGEVKNPGSVV,
   EYGFDTSDYYYYY,
   AASGFTFSSSAMSC,
   AWKYENGNDKHYADSVNG, and
   DAFPYVSPTFFAH; and
   (b) introducing said inoculum into a human whose autoimmune immunoglobulin is in need of regulation in an amount effective to interact with the immune system of said human and produce antibodies to said polypeptide.

24. The method according to claim 23 wherein said inoculum induces antibodies in said human that bind to and inactivate autoimmune immunoglobulins.

25. The method according to claim 24 wherein said autoimmune immunoglobulins are affixed to lymphocytes.

26. The method according to claim 23 wherein said inoculum induces the production of autologous T cells in said human.

27. The method according to claim 23 wherein said polypeptide is present in said inoculum as a polymer of one of said polypepties.

28. The method according to claim 23 wherein said polypeptide is present in said inoculum bound to an antigenic carrier as a conjugate.

29. The method according to claim 28 wherein said antigenic carrier is tetanus toxoid.

30. The method according to claim 28 wherein said polypeptide contains about 8 to about 20 aminio acid residues.

31. The method according to claim 28 wherein said synthetic polypeptide immunologically corresponds substantially to a primary amino acid residue sequence of an idiotypic determinant of an immunoglobulin, said idiotypic determinant including the amino acid residue sequence, taken from left to right and in the direction from amino-terminus to carboxy-terminus, represented by the formula
   YGASSRATGIPDR.

32. The method according to claim 28 wherein said synthetic polypeptide has the amino acid residue sequence, taken from left to right and in the direction from amino-terminus to carboxy-terminus, represented by the formula
   YGASSRATGIPDR.

33. A method for assaying for the presence of an idiotypic antigenic determinant of an autoimmune immunoglobulin in a sample comprising:
   (a) providing an antibody induced by a synthetic polypeptide having an amino acid residue sequence containing about 6 to about 40 amino acid residues immunologically corresponding substantially to a primary amino acid residue sequence of an idiotypic determinant of an immunoglobulin, said idiotypic determinant including an amino acid residue sequence, taken from left to right and in the direction from amino-terminus to carboxy-terminus, represented by a formula that is a member of the group consisting of
YGASSRATGIPDR,
KTSGGTFSGYTISC,
EWKGOVNVNPFDY, and
EYGFDTSDYYYYY;
- (b) admixing a predetermined amount of aid antibody with a predetermined amount of sample to e assayed for the presence of said idiotypic antigenic determinant to form an admixture;
- (c) maintaining said admixture for a period of time sufficient for said antibody to immunoreact with and to bind to an idiotypic antigenic determinant that may be present in said admixture; and
- (d) determining the amount of binding between said antibody and said idiotypic antigenic determinant of said immunoglobulin.

34. A method for assaying an idiotypic antigenic determinant of an autoimmune immunoglobulin in a sample comprising:
    - (a) providing a solid support-affixed antibodies raised in an animal host to a synthetic polypeptide having an amino acid residue sequence containing about 6 to about 40 amino acid residues immunologically corresponding substantially to a primary amino acid residue sequence of an idiotypic determinant of an immunoglobulin, said idiotypic determinant including an amino acid residue sequence, taken from left to right and in the direction from amino-terminus to carboxy-terminus, represented by a formula that is a member of the group consisting of
YGASSRATGIPDR,
KTSGGTFSGYTISC,
EWKGOVNVNPRDY, and
EYGFDTSDYYYYY;
said antibodies having the capacity of immunoreacting with said idiotypic determinant;
    - (b) providing an aliquot of said sample;
    - (c) admixing said aliquot with said antibodies to form a liquid-solid phase admixture;
    - (d) maintaining said admixture for a period of time sufficient for said antibodies to immunoreact with an idiotypic antigenic determinant that may be present in said admixture; and
    - (e) determining the amount of reaction between said antibodies and said idiotypic antigenic determinant of said immunoglobulin.

35. The method according to claim 34 wherein said solid and liquid phases are separated following step (d) and prior to step (e).

* * * * *